US008729067B2

(12) United States Patent
Garner et al.

(10) Patent No.: US 8,729,067 B2
(45) Date of Patent: May 20, 2014

(54) PHARMACOLOGICAL TREATMENT OF COGNITIVE IMPAIRMENT

(75) Inventors: Craig C. Garner, Los Altos, CA (US); Fabian J. Fernandez, Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 409 days.

(21) Appl. No.: 11/752,188

(22) Filed: May 22, 2007

(65) Prior Publication Data
US 2008/0009475 A1    Jan. 10, 2008

Related U.S. Application Data

(60) Provisional application No. 60/802,760, filed on May 22, 2006.

(51) Int. Cl.
*A01N 43/00* (2006.01)
*A61K 31/55* (2006.01)
*C07D 487/00* (2006.01)
*C07D 498/00* (2006.01)
*C07D 513/00* (2006.01)
*C07D 515/00* (2006.01)

(52) U.S. Cl.
USPC ..................... 514/214.02; 540/578

(58) Field of Classification Search
USPC ..................... 514/214.02; 540/578
See application file for complete search history.

(56) References Cited

U.S. PATENT DOCUMENTS

| | | |
|---|---|---|
| 6,277,838 B1 | 8/2001 | Upasani |
| 6,399,604 B1 | 6/2002 | Albaugh |
| 6,426,343 B1 | 7/2002 | Dawson |
| 2002/0151591 A1 | 10/2002 | Villalobos |
| 2003/0092912 A1 | 5/2003 | DeSimone |
| 2004/0023993 A1 | 2/2004 | DeSimone |
| 2004/0082555 A1 | 4/2004 | Villalobos |
| 2005/0130948 A1 | 6/2005 | Rees |

FOREIGN PATENT DOCUMENTS

| | | |
|---|---|---|
| WO | WO 99/43661 A2 | 9/1999 |
| WO | WO 2003013514 * | 7/2002 |

OTHER PUBLICATIONS

Krivanek et. al., Psychopharmacologia, 1968, Springer Berlin, vol. 12, pp. 303-321.*
Chong et. al., Brain Res. Rev., 2005, National Institutes of Health, vol. 49, No. 1, pp. 1-21.*
Guttman et. al., CMAJ, 2003, Canadian Medical Association, vol. 168, No. 3, pp. 293-301.*
Hanson et. al., BMC Medical Genetics, 2005, BioMed Central Ltd., vol. 6, No. 7, pp. 1-17.*
Tsuang et. al., Am. J. Psychiatry, 2000, American Psychiatric Association, vol. 157, No. 7, pp. 1041-1050.*
Hosie et. al., Nature Neuroscience, 2003, Nature Publishing Group, vol. 2003, pp. 362-369.*
Darbin et. al., Pharmacology, Biochemistry, & Behavior, 2002, Elsevier, vol. 71, pp. 319-324.*
Takeda et. al., J. Neurochemistry, 2003, Int. Society for Neurochemistry, vol. 85, pp. 1575-1580.*
Tanelian et. al., Anesthesiology, 1993, American Soc. for Anesthesiologists, vol. 78, pp. 757-776.*
Yamamoto et. al., Cell, 2000, Cell Press, vol. 101, pp. 57-66.*
Turkel et. al., Journal of Orthomolecular Medicine, 1986, International Society for Orthomolecular Medicine, vol. 1, No. 4, pp. 219-229.*
Lieberman, A.L., "Subconvulsive intravenous metrazol therapy in mental patients; a preliminary report", *Geriatrics*, 9(3):125-127 (1954).
Hamm, R.J. et al., :"Chronic Administration of Pentylenetetrazole after traumatic brain injury improves cognitive performance of injured rats", Society of Neurosceicen Abtracts, 24th Annual Meting of the Society *for Neuroscience*, 20(1-2):193, Abstract # 84.14 (1994).
Varvel, S.A., et al, "Delta(9)-THC-induced cognitive deficits in mice are reversed by the GABA(A) antagonist bicuculline", *Psychopharmacology*, 178(2-3):317-327 (2005).
Bauer, Richard H., "Twenty-Four Hour Proactive Facilitation of Avoidance and Discrimination by Pentylenetetrazol", *Psychopharamacologia (Berl..)*, 24:275-295 (1972).
Berman et al., "Pentylenetetrazol (Metrazol) in Mental Deficiency", *A.M.A. Journal of Diseases of Children*, 94:231-233 (1957).
Gross et al., "Oral Metrazol Therapy in Psychotic Senile and Arteriosclerotic Patients", *J. Am. Geriatr. Soc.*, 2(8):514-518 (1954).
Lu et al., "A Controlled Study of Drugs in Long-Term Geriatric Psychiatric Patients," *Arch. Gen. Psychiat.*, 25:284-288 (1971).
Lieberman, A.L., "Evaluation of Intravenous and Oral Use of Metrazol in Hospitalized Arteriosclerotic Psychiatric Patients", *Geriatrics*, 9(8):371-374 (1954).
Bumbalo, et al., "Treatment of Down's Syndrome with the 'U' series of drugs", JAMA, vol. 187, No. 5, pp. 361, (1964).
Turkel, et al., "Medical amelioration of Down's Syndrome incorporating the orthomolecular approach", Orthomolecular Psychiatry, vol. 4, No. 2, pp. 102-115 (1975).
D'Antuono, M. et al., "Letter to Neuroscience—Involvement of Cholinergic and Gabaergic Systems in the Fragile X Knockout Mice," Neuroscience, 199, pp. 9-13, (2003).

(Continued)

*Primary Examiner* — Sarah Pihonak

(57) ABSTRACT

Methods for treating an individual to improve cognitive function are provided. In the subject methods, an effective amount of a noncompetitive $GABA_A$ ionophore blocker is administered to the individual, resulting in an improvement in cognitive function of the host. The subject methods find use in a variety of different applications.

9 Claims, 13 Drawing Sheets

(56) References Cited

OTHER PUBLICATIONS

Arai et al., "Excessive glutamate receptor 1 immunoreactivity in adult Down syndrome brains", Pediatr. Neurol., 1996, 15(3):203-206.

Atack et al., "L-655,708 enhances cognition in rats but is not proconvulsant at a dose selective for alpha5-containing GABAA receptors", Neuropharmacology, 2006, 51(6):1023-1029.

Belichenko et al., "Synaptic structural abnormalities in the Ts65Dn mouse model of Down Syndrome", J Comp Neurol., 2004, 480(3):281-298.

Berman et al., "Pentylenetetrazol (metrazol) in mental deficiency", AMA J Dis. Child., 1957, 94(3):231-233.

Cocchi et al., "Height increase in children with Down syndrome following treatment with psycho-pharmacotherapeutic agents", Int J Psychosom., 1985, 32(2):12-16.

Costa and Grybko., "Deficits in hippocampal CA1 LTP induced by TBS but not HFS in the Ts65Dn mouse: a model of Down syndrome", Neurosci. Lett., 2005, 382(3):317-322.

Donfrancesco and Dell'Uomo, "Ginkgo biloba in Down Syndrome", Phytomedicine, 2004, 11(6):469.

Ivic et al., "Terpene trilactones from Ginkgo biloba are antagonists of cortical glycine and GABA(A) receptors", J Biol Chem, 2003, 278(49): 49279-4928.

Kleschevnikov et al., "Hippocampal long-term potentiation suppressed by increased inhibition in the Ts65Dn mouse, a genetic model of Down syndrome", J Neurosci., 24(37):8153-8160, (2004).

Kurt et al., "Synaptic deficit in the temporal cortex of partial trisomy 16 (Ts65Dn) mice", Brain Res., 2000, 858 (1):191-197.

Levkovitz et al., "Upregulation of GABA neurotransmission suppresses hippocampal excitability and prevents long-term potentiation in transgenic superoxide dismutase-overexpressing mice", J Neurosci., 1999, 19(24):10977-10984.

Solomon et al., "Ginkgo for memory enhancement: a randomized controlled trial", JAMA, 2002, 288(7):835-840.

Stotsky et al., "A controlled study of the efficacy of pentylenetetrazol (Metrazol) with hard-core hospitalized psychogeriatric patients", Am J Psychiatry, 1972, 129(4):387-391.

* cited by examiner

FIG. 7
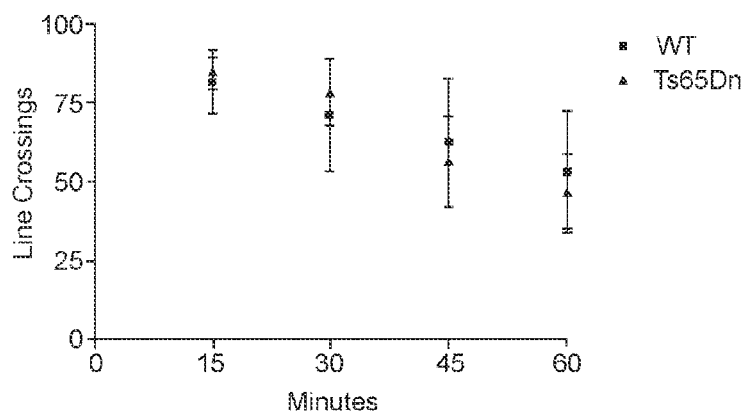
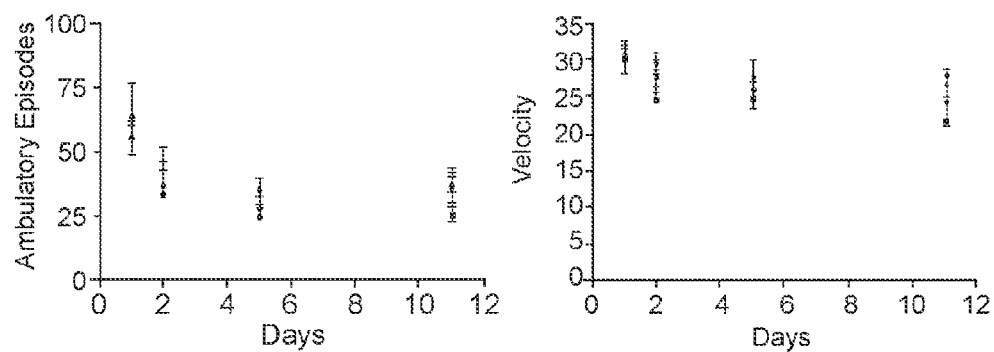

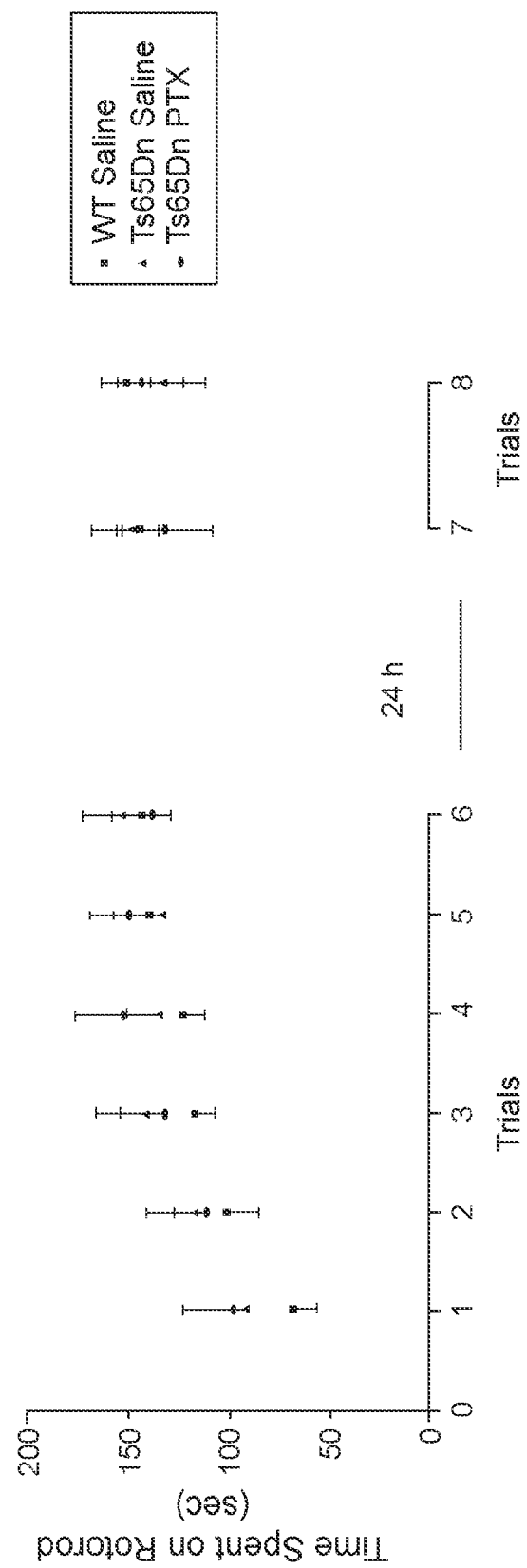

PHARMACOLOGICAL TREATMENT OF COGNITIVE IMPAIRMENT

CROSS-REFERENCE TO RELATED APPLICATIONS

This applications claims benefit of priority to U.S. provisional application 60/802,760, filed May 22, 2006, which is herein incorporated by reference.

BACKGROUND OF THE INVENTION

Mental retardation (MR) affects 2-3% of the population in the industrialized world, and remains a prevalent form of non-progressive cognitive impairment. Narrowly defined by an IQ of less than 70 and deficits in academic, adaptive, and interpersonal skills, disorders involving MR are, nonetheless, spread over a broad etiology, resulting from both genetic and non-genetic causes. The breadth and frequency of MR-related cognitive dysfunction is alarming considering that pharmacological intervention is currently non-existent.

Historically, neuroscientists have probed the brain in MR for clues to possible treatment strategies of MR-related learning difficulties. In the case of Down syndrome, these pioneering investigations have led to observations of tissue atrophy, white matter abnormalities, neuronal cell loss, stunted dendritic branching, and spine dysgenesis. Interestingly, many of the histological features noted in the brains of individuals with Down syndrome parallel phenotypes that have been found in the brains of individuals with other classes of MR, such as inborn errors of metabolism and non-genetic insults. Connections among different X-linked forms of MR have also been made, with disrupted synaptic structure, synaptic plasticity, and Ras-MAPK signaling as emerging themes. Similarities across the wide spectrum of MR-related disorders argue that common mechanisms underlie the manifestation of learning and memory deficits in intellectually handicapped children and young adults.

Down Syndrome (DS) is the most commonly occurring form of mental retardation in man, with an incidence of 1 in 600 births. The etiology surrounding the disorder was first described as a nondisjunctive error during meiosis of human chromosome 21 (hC21), resulting in the overexpression of an estimated 225 genes normally found on the chromosome. DS is characterized by congenital heart disease, endocrine disturbances, and immunologic deficiency, but is most universally marked by learning and memory difficulties in affected individuals that preclude adaptive cognitive and interpersonal function.

How the presence of hC21 genes in triplicate alters the maturation of the central nervous system (CNS) and subsequent cognitive development in DS has remained an open question. DS brains generally appear normal at birth. Newborns with DS exhibit typical brain weights, and do not exhibit any differences in gross neuronal and synaptic structure from children without the disorder. Quantitative analysis of DS prefrontal layer III pyramidal cells around birth and at 2.5 months of age indicates no differences in dendritic differentiation. Brain growth, in fact, proceeds normally for the first 5 to 6 months of life. However, soon after the infantile period (>6 months) the DS brain begins to show the abnormalities that characterize it in adulthood. The emergence of these cytological abnormalities may coincide with the beginning of IQ decline in DS-affected children within the first few years of life.

Investigation of CNS abnormalities and cognitive dysfunction in DS has been greatly facilitated by the development of two segmentally trisomic mouse models of DS: Ts65Dn and Ts1Cje. Ts65Dn mice are trisomic for segments of mouse chromosome 16 (Mmu 16) highly homologous to the long arm of hC21, including portions of the so-called DS "critical region." Phenotypically, Ts65Dn mice faithfully recapitulate some of the most salient and fundamental features of DS. The topography of craniofacial maldevelopment in Ts65Dn mirrors that observed in DS patients; likewise, Ts65Dn mice exhibit similar patterns of cerebellar atrophy during early postnatal development. The utility of Ts65Dn as a mouse model of DS is strengthened further by findings that detail nearly comprehensive deficits in Ts65Dn short- and long-term spatial memory, working memory, and reference memory.

The treatment of mental retardation is of great clinical and humanitarian interest. The present invention addresses this issue.

Publications

The synaptic connections in the Ts65Dn brain have been assessed by a variety of assays. For example, quantitative electron microscopy (EM) of Ts65Dn CNS has revealed a loss of asymmetric, excitatory synapses in Ts65Dn cortex relative to WT tissue, with a concurrent sparing of symmetric, inhibitory synapses (Kurt et al., 2000). Reductions in the density of excitatory synapses, and in the ratio of excitatory-to-inhibitory signaling in the Ts65Dn brain, have been noted alongside compensatory increases in the synaptic apposition lengths of asymmetric and symmetric synaptic junctions.

Recent studies using lucifer-yellow filling of neurons in Ts65Dn acute slices have indicated that a widening of synaptic clefts may relate to the development of enlarged spines in Ts65Dn cortex (see Belichenko et al. (2004) J Comp Neurol. 480(3):281-98). In an in vitro system, deficits in Ts65Dn hippocampal LTP were shown to reverse upon application of picrotoxin (see Kleschevnikov (2004) J. Neurosci. 24(37): 8153-60). Costa et al., (2005) Neur. Lett. 382:317-322 report deficits in hippocampal CA1 LTP induced by TBS but not HFS in the Ts65Dn mouse. Levkovitz et al. (1999) J. Neuroscience 19:10977-10984 discuss upregulation of GABA neurotransmission in the suppression of hippocampal excitability and prevention of long-term potentiation in transgenic superoxide dismutase-over-expressing mice.

It has been suggested that excessive immunoreactivity of the glutamine receptor GluR1 may be involved in degeneration of neurons and the early formation of senile plaques in Down syndrome, as tissue samples taken from the frontal lobes of patients with Down syndrome exhibit homeostatic elevations in GluR1 immunoreactivity (Arai et al. (1996) Pediatr. Neurol. 15:203-206).

*Ginkgo biloba* extract was administered to two young patients with trisomy 21 (Donfrancesco et al. (2004) Phytomedicine 11:469. Pentylenetetrazol (metrazol) was administered to children with mental deficiencies by Berman et al. (1957) AMA Journal of Diseases of Children 94:231; and to psychogeriatric patients by Stotsky et al., (1972). GABAergic agonist (diazepam) drugs were administered to children with Down Syndrome by Cocchi (1985) Int. J. Psychosomatics 32:12-16 reducing depression.

Heteroaryl fused aminoalkyl-imidazole derivatives as selective modulators of GAGAA receptors are discussed in US Patent Application 2003/0092912. Use of GABA inverse agonists in combination with nicotine receptor partial agonist, estrogen, selective estrogen modulators or vitamin E is discussed in U.S. Patent Application 2004/0082555. Combination use of acetylcholinesterase inhibitors and $GABA_A$ inverse agonists for the treatment of cognitive disorders is discussed in U.S. Patent Application 2002/0151591. L-655, 708 is reported to enhance cognition in rats but is not proconvulsant at a dose selective for α5-containing $GABA_A$ receptors.

SUMMARY OF THE INVENTION

Methods are provided for improving the cognitive function of an individual suffering from mental retardation. The individual is administered an effective, non-epileptic dose of a $GABA_A$ receptor chloride ionophore blocker, for a period of time sufficient to improve cognitive function. Long term cognitive improvement can be obtained from the methods of the invention, which can persist after cessation of treatment. Conditions of interest for treatment include Down Syndrome, and other congenital or acquired conditions that impair cognitive function. Also provided are kits for use in practicing the subject methods.

In another embodiment of the invention, methods are provided for screening drug candidates for effectiveness in treating cognitive impairment associated with mental retardation. Such methods may include screening assays with animal or cell models, and may include a comparison with a reference value obtained from known $GABA_A$ receptor chloride ionophore blockers. Screening may be used to identify agents that selectively target specific cells to improve targeting specificity of the intervention.

BRIEF DESCRIPTION OF THE FIGURES

FIG. 12. Motor Learning in WT and Ts65Dn Mice: Chronic PTX Treatment does not influence Ts65Dn Rotorod Performance.

DESCRIPTION OF THE SPECIFIC EMBODIMENTS

Figure 1:
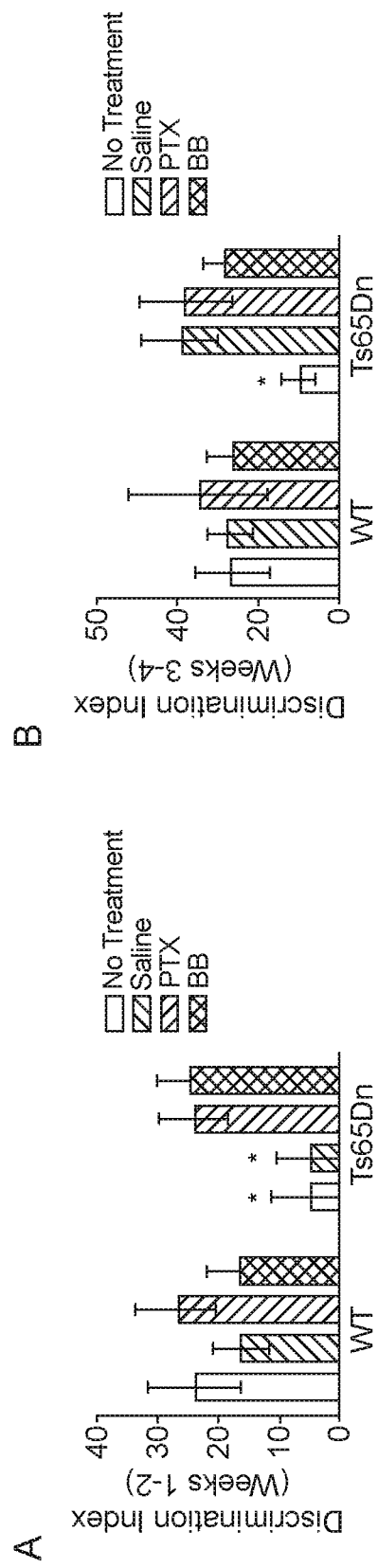
FIG. 1A-1B. Chronic Administration of PTX or BB Rescues and Maintains Ts65Dn Object Recognition Memory.

The cognitive function of an individual suffering from mental retardation is alleviated by administration of a $GABA_A$ receptor chloride ionophore blocker for a period of time sufficient to improve cognitive function. Cognitive improvement is provided by "therapeutic kindling" of neural circuits, and is achieved by administering the active agent at very low, non-epileptic, doses, which in one embodiment of the invention are administered not more than about once a day; and/or which can administered with a sleep period between doses. In other embodiments of the invention, a very low dose is administered, which is optionally provided in a continuous dosing regimen. The dosing regimen is usually maintained for at least about one week, at least about two weeks, at least about three weeks, at least about one month, or more. In some embodiments of the invention, the active agent is fast acting and short lived. In some embodiments of the invention, the active agent is non-competitive in character and is not selective for a specific $GABA_A$ alpha subunit, e.g. α1, α5, etc.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

γ-Aminobutyric acid (GABA) is the major inhibitory neurotransmitter in the mammalian central nervous system. The predominant effect of GABA is the interaction with a specific receptor protein which results in an increase of the chloride ion conductance of the post-synaptic membrane to produce an inhibition of neuronal firing. In recent years, much attention has been focused on this specific receptor, the $GABA_A$ receptor.

As shown in the examples provided herein, decreased functionality in cognitive performance of an individual suffering from mental retardation can be associated with increased inhibition in the brain. Treatment by chronically administering low doses of drugs that globally reduce chloride influx mediated by $GABA_A$ channels is shown to improve cognitive function. Compounds of interest specifically reduce the activity of $GABA_A$ receptors via block of the $GABA_A$ receptor-chloride ionophore complex. Detailed studies with three different $GABA_A$ antagonists within this class, in a model of Down syndrome, reveal that normal cognitive performance can be achieved after long-term administration of these drugs, demonstrating their utility as a treatment for Down syndrome, and other forms of mental retardation.

Neurite outgrowth and on-going synaptogenesis are critically influenced by the balance of circulating glutamate and GABA during development of the cerebral cortex. During the early phases of neurite outgrowth, GABA acts like an "excitatory" agent in the brain, as the neuronal chloride gradient in maturing cells is reversed; facilitating neuronal calcium entry, and positively regulating neurite extension. GABA's traditional role as an inhibitory transmitter in the brain emerges during the activity-dependent refinement of cortical circuits, entailing the pruning of arbors in the outer fringes of the dendritic field and the strengthening of remaining synaptic connections.

Molecular cloning data indicate that the $GABA_A$-benzodiazepine receptor complex is comprised of at least five subunits; these in turn may have various isoforms. Each subunit is comprised of four membrane-spanning regions. The intracellular loops of some subunits contain phosphorylation sites, which have been hypothesized to be a locus of receptor modulation. A complete system of α, β, and γ subunits are needed for a fully responsive receptor.

At least four interacting allosteric drug binding sites are known to occur within this receptor. These include those for the site of action of the tranquillizer drugs, the benzodiazepines, the neurosteroids, and barbiturates. These sites correspond to the binding sites for benzodiazepines, for GABA, for steroids, and for picrotoxin. The various types of drug binding site on the $GABA_A$ receptor may allosterically interact with each other. Compounds that bind to any one of these sites may have agonist, reverse agonist, or antagonist activity. Uniquely, opposing pharmacological actions appear to be mediated through this one receptor protein. Thus compounds which interact at the benzodiazepine site can be anxiolytic, or conversely they can have anxiogenic and convulsant properties.

Compounds of interest for use in the methods of the invention specifically block the chloride ionophore site of $GABA_A$, and are antagonists, i.e. reduce chloride influx. In some embodiments of the invention, the therapeutic compound is a non-competitive antagonist at the GABA-A receptor that binds to a chloride ionophore pore forming region of the receptor to interfere with chloride conductance; it does not interfere with GABA transmitter binding, nor does it allosterically modulate the receptor. Picrotoxin, Metrazol and bilobalide have been shown to function in this manner. Suitable $GABA_A$ receptor chloride ionophore blockers that may be used in the subject methods include, but are not limited to: metrazol; picrotoxin, bilobamide, ginkgolide B, penicillin, etc.

Compounds of interest for use on the methods of the invention may have epileptic activity, and therefore the dose is carefully selected. A compound of interest is administered at a dose below the dose that will kindle seizures. Such a "low" dose is usually less than about 0.5× the kindling dose, more usually less than about 0.1× the kindling dose, less than about 0.05× the kindling dose; less than about 0.01× or less than about 0.005× the kindling dose. The determination of a kindling dose for an agent of interest may be empirically determined, e.g. in an animal model, or may be based on known kindling dosage. For example, the effect of pentylenetetrazole in kindling is well-known in the art. In some embodiments of the invention an effective dose will at least transiently alter the chloride influx at $GABA_A$ receptors in the central nervous system, i.e. for a period of at least about 1 minute, at least about 5 minutes, at least about 30 minutes, at least about 1 hours, or more, usually not more than about 4 hours; not more than about 3 hours; not more than about 2 hours.

However, there may also be embodiments where the effective dose provides for a longer lasting effect, for example where the dose, e.g. a very low dose, provides for a longer lasting alteration of calcium influx at $GABA_A$ receptors in the central nervous system, e.g. for at least about 12 hours, at least about 24 hours, or longer. Such embodiments may utilize doses that are less than about 0.05× the kindling dose; less than about 0.01× or less than about 0.005× the kindling dose. In such embodiments the dosing may provide for a more continuous activity profile, e.g. where an effective dose of the agent is provided with a continuous pump, or is administered more than once a day, e.g. twice, 3 times, 4 times per day, and the like.

Pentylenetetrazole is a pharmaceutical agent that displays activity as a central nervous system and respiratory stimulant. It is considered a non-competitive GABA antagonist. Pentylenetetrazole has been used experimentally to study seizure phenomenon and to identify pharmaceuticals that may control seizure susceptibility. In the class of drugs exemplified by pentamethylenetetrazol (also referred to as metrazol). An effective dose may range from at least about 0.1 mg/kg, at least about 0.2 mg/kg, at least about 0.5 mg/kg, at least about 1 mg/kg to not more than about 2, about 2.5, or about 3 mg/kg. The compounds are orally active, and cross the blood brain barrier.

Related compounds may also be of interest, for example where one or more annular carbons of the 7-membered ring are optionally substituted with a lower alkyl of from 1-6 carbon atoms, a hydroxyl group, a sulfhydryl group, an amine or substituted amine, a nitro group, Br, Cl, F, I, and the like.

Pentylenetetrazol has been demonstrated to facilitate normal learning and memory in rats and mice when administered acutely post-training (peripheral injection or oral intake) in avoidance- and discrimination-based tasks. Chronic subcutaneous administration of the drug in a relatively high dose (at approximately 10.0 mg/kg) to rats for ~9 months curtails signs of neuronal aging in the hippocampus; long-term Metrazol treatment preserves hippocampal neuronal density and nuclear "roundedness," reduces the appearance of reactive astrocytes, and elevates reversal learning in a shock-motivated, spatial maze task.

There is no critical period for Metrazol-guided changes in brain circuitry; it can occur in the young, as well as in the aged. Metrazol has a long history of clinical usage in humans, showing a mixed ability to treat age-related senility and dementia. Metrazol, when taken at a dose range of less than about 100-400 mg/day, possesses little to no adverse or toxic effects. Patients on Metrazol exhibited no changes in temperature curves, respiration, blood sugar, icteric index or pulse rate, and exhibited no abnormalities in their electrocardiographic tracings. Basic personality structure and reaction patterns were also conserved in those taking the drug.

Radioactive studies with $C^{14}$ and HPLC analysis demonstrate that Metrazol is fast acting, and is very rapidly adsorbed after oral intake or systemic injection (maximum physiological levels being achieved within 5-10 min of drug administration), readily crosses the blood-brain barrier, and partitions seamlessly between blood serum and brain, soon reaching an equilibrium between both compartments where the volume of distribution approximates the volume of total body water. Similarly, kinetic patterns within various brain regions after intraperitoneal injection (half-life absorption phase, half-life distribution phase, half-life elimination phase, etc) indicate that Metrazol is allocated evenly between the 3 major brain divisions: cerebellum, midbrain and the cortex. Subsequently, the main elimination pathway of the drug is biotransformation in the liver and urinary excretion. Metrazol is short-lived, where the half-life has been estimated to be 1-2 h.

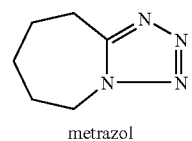

metrazol

Picrotoxin is a noncompetitive antagonist at GABA-A receptors, and has been classified as a convulsant. Picrotoxin blocks the GABA-activated chloride ionophore. It has been used as a CNS stimulant and an antidote in poisoning by CNS depressants, especially the barbiturates. Picrotoxin and related compounds are administered at an effective dose that may range from at least about 0.5 mg/kg, to not more than about 1 mg/kg. A kindling dose may be as little as 2.0 mg/kg, or 1.5 mg/kg. The compounds may be administered systemically, usually by injection.

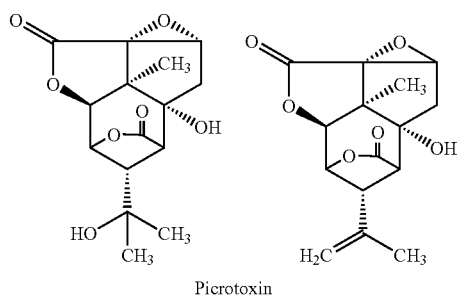

Picrotoxin

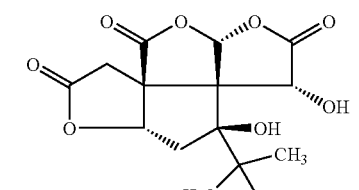

Bilobalide

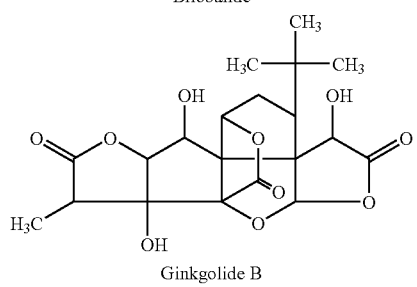

Ginkgolide B

Bilobalide and ginkgolide B comprise part of a novel class of compounds called terpene trilactones, unique constituents of *Ginkgo Biloba* that are found exclusively in the *Ginkgo Biloba* tree. The compounds function as potent non-competitive antagonists at GABA-A receptors, acting as open-channel blockers of the chloride ionophore associated with the receptor complex. Consistent with this pharmacological action, bilobalide has been shown to significantly increase the amplitude of hippocampal population spikes in a muscimol-dependent manner, and to decrease paired pulse inhibition. Additionally, both bilobalide and Ginkgolide B have been demonstrated to shorten sleeping time during barbital-induced narcosis. As constituents of *Ginkgo Biloba*, they, likewise, activate the EEG, enhance the pro-convulsant effects of PTX, and trigger seizures in refractory epilepsy.

Pharmacokinetic studies in humans reveal that bilobalide is 70% bioavailable after oral intake of a 80-120 mg dose of *ginkgo biloba* leaf extract (with a half-life of 3 h), while that of Ginkgolide B is at least 80% (with a half-life of 6 h). In this form, approximately, 30-50% of bilobalide and ginkgolide B is excreted unchanged in the urine. To date, a systematic pharmacokinetic evaluation of bilobalide or ginkgolide B following oral administration of purified compound remains to be conducted. However, the terpene trilactones' amphiphilic behavior suggests that they would accumulate particularly well in brain tissue after passing through the blood brain barrier (BBB). Clinical studies evaluating the terpene trilactones are very limited. However, to date, no serious side effects have been reported for ginkgolide B during clinical trials designed to evaluate the drug's efficacy in treating allergy (asthma, skin disorders), burn injury, sepsis, and blood clotting.

A pharmaceutical formulation of bilobalide or ginkgolide B is substantially free of other pharmaceutically active agents presents in *Ginkgo biloba* extracts, particularly being substantially free of ginkgolytic acids. In such pharmaceutical formulations, the desired active agent, i.e. bilobalide or ginkgolide B may be at least about 50% of the *Ginkgo biloba*-derived material, usually at least about 75% of the *Ginkgo biloba*-derived material, at least about 85% of the *Ginkgo biloba*-derived material, at least about 95% of the *Ginkgo biloba*-derived material, or more. As known in the art, a pharmaceutical formulation may comprise pharmaceutically acceptable excipients and carriers.

An effective dose of bilobalide or ginkgolide B may range from at least about 0.1 mg/kg, at least about 0.2 mg/kg, at least about 0.5 mg/kg, at least about 1 mg/kg to not more than about 5 mg/kg, not more than about 2.5 mg/kg. The compounds are orally active, and cross the blood brain barrier.

Conditions of Interest

Various forms of MR may be attributed to the over-inhibition of cortical circuits, resulting in major homeostatic disturbances in circuit activity that underlie learning and memory. By inhibition of $GABA_A$ for an effective period of time at a non-epileptic dose, over-inhibition is relieved, allowing for long term changes to neuronal interactions. A number of conditions may be treated by the methods of the invention. Such conditions include, without limitation, those listed below.

Down Syndrome.

Down syndrome is the most frequent genetic cause of mild to moderate mental retardation and associated medical problems and occurs in one out of 800 live births, in all races and economic groups. Down syndrome is a chromosomal disorder caused by the presence of an additional third chromosome 21 or "trisomy 21." Three genetic variations can cause Down syndrome. In approximately 92% of the time, Down syndrome is caused by the presence of an extra chromosome 21 in all cells of the individual. In approximately 2-4% of cases, Down syndrome is due to mosaic trisomy 21, and the remaining cases result from a translocation trisomy 21.

Most people with Down syndrome have IQ's that fall in the mild to moderate range of retardation. Premature aging is a characteristic of adults with Down syndrome. In addition, dementia, or memory loss and impaired judgment similar to that occurring in Alzheimer disease patients, may appear in adults with Down syndrome. This condition often occurs when the person is younger than forty years old.

Observations of patients with DS suggest that imbalances in GABAergic and glutamatergic transmission, favoring a greater efficacy of GABAergic signaling, may be present during initial neurological developmental events. The methods of the invention demonstrate that targeted pharmacological intervention with GABA-A receptor antagonists can result in lasting increases in circuit excitability, and improvement in adult learning and memory.

Phenylketonuria is a mental retardation disorder caused by the deficiency of the hepatic enzyme phenylalanine-4 hydroxylase and the build-up of CNS phenylalanine. L-phenylalanine at concentrations observed in untreated PKU depresses the amplitude and frequency of both NMDA and non-NMDA components of mEPSP's in dissociated cortical cultures. Mechanistically, these effects are mediated in large part by phenylalanine's competitive antagonism of the obligatory agonist site of the NMDA receptor, but may involve other postsynaptic and presynaptic mechanisms as well. Golgi studies performed on children with PKU reveal a prevalence of immature dendritic spines in pyramidal cells of the cerebral cortex.

Neonatal Protein Malnutrition.

Non-genetic forms of cognitive impairment can be induced by protein or caloric malnutrition. Morphological hallmarks of excessive inhibition can be observed in the cerebral cortex of malnourished individuals, with the proliferation of unusually long, narrow spines.

Fragile X Syndrome.

MR syndromes brought about by specific deficits in neuronal signal transduction provide evidence for excessive inhibition as a major contributing factor to cognitive dysfunction. Fragile X syndrome is due to a trinucleotide repeat expansion in the FMR1 gene that prevents expression of its encoded protein product—fragile X mental retardation protein (FMRP). X-linked mental retardation associated with marXq28, or fragile X syndrome, is characterized by moderate to severe mental retardation, macroorchidism, large ears, prominent jaw, and high-pitched jocular speech. Expression is variable, with mental retardation being the most common feature.

Cortical cultures in an animal model of Fragile X syndrome display delayed formation and maturation of neuronal network activity, and decreased BDNF expression compared to cultures prepared from wild-type (WT) littermates. These animals also show scaled reductions in cortical and hippocampal $GABA_A$ receptor subunit immunoreactivity, and increases in olfactory bulb GluR1 immunoreactivity. Complementing these electrophysiological findings are studies documenting a higher density of unusually long dendritic spines in fragile X patients.

Neuroimaging studies using fMRI have shown that FMRP levels are positively correlated with activation of the prefrontal cortex in individuals with fragile X during performance of a working memory task. These results suggest that FMRP is required during especially demanding cognitive exercises, and that failure to meet these demands with appropriate concentrations of FMRP result in decreased network activity. FMRP's role as a regulator of site-specific protein translation in dendritic spines may account for many of the observations that have been made in fragile X patients and in animal models of the disorder.

Neurofibromatosis 1.

This condition is attributed to genetic mutations in the NF1 gene and loss of function of neurofibromin's ras guanosine triphosphatase (rasGAP) activity, presents the most direct link between overinhibition in the brain and mental retardation. Animals carrying a heterozygous null mutation of the NF1 gene ($Nf1^{+/-}$) exhibit spatial learning deficits in the Morris water maze that intimately relate with increases in GABA-mediated inhibition. $Nf1^{+/-}$ mice have larger mIPSP's and evoked IPSP's than WT controls, and decreases in hippocampal LTP. Thus, partial loss of neurofibromin's rasGAP activity, and subsequent unregulated ras activation, leads to abnormally high GABA-mediated inhibition, which underlies impairments in Hebbian plasticity and learning and memory. This devastating cascade of events can be prevented by administration of farnesyl transferase inhibitors, anti-ras agents, which return learning and memory in $Nf1^{+/-}$ adult mice to control levels.

Maple Syrup Urine Disease is a mental retardation disorder resulting from the loss of function of the branched chain L-α-keto acid dehydrogenase complex and a subsequent accumulation of the metabolic substrates α-ketoisocaproic acid (KIC), α-keto-β-methylvaleric acid (KMV), and α-ketoisovaleric acid (KIV). Experiments have shown that α-keto acids dampen cortical excitation and reduce learning in a dose-dependent fashion. Administration of physiologically relevant concentrations of KIV to dissociated cortical neurons significantly reduces spontaneous network activity, while intra-hippocampal infusion of KIC, KMV and KIV severely disrupts the acquisition of an inhibitory avoidance task. The effects of α-keto acids on cortical activity and cognition appear to be mediated via direct interactions of the metabolites with the vesicular glutamate transporter. Application of α-keto acids inhibits glutamate uptake into synaptic vesicles in a competitive manner and changes the chloride dependence for the activation of vesicular glutamate transport. Alpha-keto acid inhibition of the vesicular glutamate transporter is dramatic during the acute phase of MSUD]. Young children with MSUD demonstrate changes in neuronal morphology, exhibiting a conspicuous abundance of long, thin dendritic spines in the cerebral cortex.

Autism, often referred to as autistic disorder or infantile autism, is a complex behavioral disorder which, by definition, develops prior to age three years. Autism is defined completely on the basis of impairments in social interaction, impairments in communication, and repetitive and stereotypic behaviors. For most children, the onset of autism is gradual; however, approximately 30% have a "regressive" onset. Fifty to seventy percent of children with autism are defined as mentally retarded by nonverbal IQ testing. Seizures develop in approximately 25% of children with autism.

The standard diagnostic criteria for autism, compiled by the American Psychiatric Association Manual of Psychiatric Diseases, 4th edition (DSM-IV), are the primary diagnostic reference used in the United States. The causes of autism can be divided into "idiopathic," which comprises the majority of cases, and "secondary," in which an environmental agent, chromosome abnormality, or single-gene disorder can be identified.

The standard diagnostic criteria include qualitative impairment in social interaction, as manifested by at least two of the following; qualitative impairments in communication; stereotyped and repetitive use of language or idiosyncratic language; lack of varied, spontaneous make-believe play or social imitative play appropriate to developmental level; restricted repetitive and stereotyped patterns of behavior, interests, and activities. Criteria also include delays or abnormal functioning in at least one of the following areas, with onset prior to age three years: social interaction, language as used in social communication, or symbolic or imaginative play Impairment in social interaction separates individuals with autism from the people around them. Children with autism are unable to "read" other people, ignoring them and often strenuously avoiding eye contact. Most children with autism fail to develop reciprocal communication either by speech, gestures, or facial expressions. Deficits in pragmatic skills are present throughout life and affect both language and social interaction. In contrast to the child with nonspecific mental retardation or a primary developmental language disorder, who usually has better receptive than expressive language, the child with autism has impaired receptive language. Fifty to seventy percent of autistic children are defined as mentally retarded by nonverbal IQ testing.

Children with Down syndrome have autism more commonly than expected. The incidence was at least 7% in one study. This finding suggests that chromosome abnormalities may lower the threshold for the expression of autism.

Whereas a very small percentage of children with autism have fragile X syndrome, at least half of children with fragile X syndrome have autistic behaviors, including avoidance of eye contact, language delays, repetitive behaviors, sleep disturbances, tantrums, self-injurious behaviors, hyperactivity, impulsiveness, inattention, and sound sensitivities.

One of the DSM-IV-defined pervasive developmental disorders, Rett syndrome exhibits considerable phenotypic overlap with autism; children with both disorders often have a period of normal development followed by loss of language with stereotypic hand movements. Decreasing rate of head growth over time and hand-wringing in female individuals may suggest the diagnosis of Rett syndrome. Molecular genetic testing for MECP2 mutations that cause Rett syndrome is clinically available. Only 1% of individuals with the diagnosis of autism have been reported to have a MECP2 coding region mutation, however these two disorders may be causally related based on reports of variants in the 3'-UTR of MECP2 in three of 24 individuals with autism and variable MeCP2 expression in the brains of individuals with both Rett syndrome and autism.

Assessment

By mental retardation is meant a cognitive impairment with a pattern of persistently slow learning of basic motor and language skills during childhood, and a significantly below-normal global intellectual capacity as an adult. One common criterion for diagnosis of mental retardation is a tested intelligence quotient (IQ) of 70 or below. Conditions of interest for treatment include Down Syndrome, and other congenital or acquired conditions that impair cognitive function. Included in the conditions of interest for treatment are those in which there is an impairment, often from early childhood, of at least one cognitive function, such as a impairment in memory, impairment in learning ability, etc.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as impairment in memory or learning ability or other cognitive function. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

As mentioned above, in these applications an effective amount of $GABA_A$ receptor chloride ionophore blocker is administered to the host. By "effective amount" is meant a dosage sufficient to produce a desired result, where the desired result is generally an amelioration or alleviation, if not complete cessation, of one or more symptoms of the disease being treated, particularly the cognitive impairment symptoms, e.g., memory, learning ability, and the like.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

In addition to the above methods of treatment, the subject methods also find use in the prophylactic or preventative treatment regimens. In such methods, the host is administered an amount of a direct $GABA_A$ inhibitor, typically according to a dosage schedule (e.g., daily, weekly, monthly etc.), that is sufficient to prevent the occurrence of at least symptoms of the disorder, e.g., impaired cognition.

In the treatment of a patient, assessment will usually include a clinical history and the collection of standardized information. Assessment may also include IQ testing. In animal models, a variety of standardized tests may be utilized for evaluation of learning and memory. Examples include analysis of sustained and non-sustained attention and impulsivity, e.g. acquisition inhibitory avoidance responding; 5-choice serial reaction time testing in rodents and a distractor version of a Delayed Match to Sample test in monkeys. Analysis of social and working memory may include social recognition model; spatial working memory using a water maze in rats; and spontaneous alternation Y mazes. Mazes, e.g. water maze with a hidden platform; 2-choice visual discrimination water maze; "dry land" Barnes circular maze; etc. are useful in testing spatial reference memory. Different configurations of the water maze measure different forms of learning and utilize different brain systems. A second commonly used paradigm for studying learning and memory is the conditioned fear test. The direct measure of freezing behavior in response to discrete conditioned stimuli such as tones or lights as a measure of learning can evaluate two discrete forms of learning, cued and contextual. A passive avoidance model is useful in assessing recall.

Many assessment tests are available. For example, memory, attention and executive function (planning abilities) can be assessed by direct testing with the participants using the DAME battery. The DAME battery has been validated as a measure that is sensitive to change in older people with Down's syndrome. The range of scores is 0-241 and can be completed in 45 minutes by most people with mild-moderate learning disability.

Independent functioning can be evaluated using the Adaptive Behavioural Scale (ABS, Nihira, 1974). This is an informant based instrument and is part of the assessment used by the American Association on Mental Deficiency to assess daily living skills in people with learning disabilities. The ABS measures ten groups of skills related to self-care and socialization. The ten skills groups: independent functioning, physical development, economic activity, language development, numbers and time, domestic activity, vocational activity, self-direction, responsibility, and socialization.

The Clinician's Global Impression of Change (CGI/C) has been one of the most commonly used test to assess overall change in clinical trials. The validity of this type of measure is based on the ability of an experienced clinician to detect clinically relevant against trivial change in a patient's overall clinical state.

In certain situations, treatment according to the subject methods results in a complete removal of a deficit in the cognitive function. The amount of improvement is at least about 2 fold, usually at least about 5 fold and more usually at least about 10 fold as compared to a suitable control, e.g., an otherwise substantially identical host not administered a $GABA_A$ receptor chloride ionophore blocker, e.g., a host having similar level of cognitive ability that has been administered a placebo, where in certain embodiments the amount of improvement is at least about 25 fold, 50 fold, 75 fold, 100 fold or greater. The cognitive function improvement can be evaluated using any convenient protocol, where suitable protocols include, but are not limited to: Wechsler Adult Intelligence Scale (WAIS_-R) [Wechsler, D. WAIS-R Manual. New York: Psychological Corporation, 1981; Mini-Mental State Examination (MMSE) [Folstein et al. Mini Mental State: a practical method for grading the cognitive state of patients for the clinician. J Psychiat Res 1975; 12:189-98; Information-Memory-Concentration test; Fuld Object Memory Evaluation (FOSE) [Fuld, P A. The Fuld Object Memory Test. Chicago: The Stoeltimg Instrument Company, 1981]; The Buschke Selective Reminding Test (BSRT) [Buschke, H. Selective reminding for analysis of memory and learning. J Verbal Learn Verb Behav 1973; 12:543-50]; The Rey Auditory Recall Test [Buschke, H. Selective reminding for analysis of memory and learning. J Verbal Learn Verb Behav 1973; 12:543-50]; The Beton Visual Retention Test (BVRT) [Benton, A L. The revised visual attention test, $4^{th}$ edn. New York: Psychological Corporation, 1974]; The California Verbal Learning Test [Delis et al. The California Verbal Learning Test. New York: Psychological Corporation, 1987]; Assessment of navigation in humans [Maguire et al. Knowing where and getting there; a human navigation network [Science 1998; 280:921-924]; and the like.

Methods

In the broadest sense, methods are provided for improving a cognitive function in a mammalian host. The host is generally a mammal, e.g. mouse, rat, monkey, etc. and in many embodiments is a human. The $GABA_A$ receptor chloride ionophore blocker is administered at regular intervals, usually at least weekly, more usually daily, or every two days, and usually with a sleep period between doses. Typically, the active agent is fast acting, and after administration the blocker reaches therapeutic levels across the blood brain barrier at least transiently, e.g. for around about 1 minute, at least about 5 minutes, at least about 30 minutes, at least about 1 hour, or more. It is not believed to be necessary to maintain such levels throughout the treatment period, as effective treatment is observed even with compounds have a short half-live after administration. The agent may be short lived, where half-life in the blood is less than about 4 hours, less than about 3 hours, less than about two hours.

Administration of the treatment is maintained for a period of time sufficient to effect a change in cognitive function. Such treatment may involve dosing for at least about one week, at least about two weeks; at least about 3 weeks; at least about one month; at least about two months; at least about four to six months; or longer, for example at least about one or more years. For extended treatment; e.g. treatment of one or more years, a schedule may involve intermittent periods, such as one week on and one week off; two weeks on and two weeks off; one week in a month, etc.

Patients that can benefit from the present invention may be of any age and include adults and children, e.g. young adults. Children, e.g. neonate, infant, early childhood, adolescent, etc. in particular may benefit prophylactic treatment. Children suitable for prophylaxis can be identified by genetic testing for predisposition, e.g. by chromosome typing; by family history, or by other medical means. As is known in the art, dosages may be adjusted for pediatric use.

The $GABA_A$ receptor chloride ionophore blocker is generally administered to the host as a pharmaceutical composition that includes an effective amount of the $GABA_A$ receptor chloride ionophore blocker in a pharmaceutically acceptable vehicle. In the subject methods, the active agent(s) may be administered to the host using any convenient means capable of resulting in the desired improvement on cognitive function.

Therapeutic agents can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intrathecal, nasal, intracheal, etc., administration. The active agent may be systemic after administration or may be localized by the use of regional administration, intramural administration, or use of an implant that acts to retain the active dose at the site of implantation.

Many $GABA_A$ receptor chloride ionophore blockers are known to be bioactive in the central nervous system after oral or parenteral administration. For those that are not, one strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents is also an option. A BBB disrupting agent can be co-administered with the therapeutic compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant for example.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

Toxicity and therapeutic efficacy of the active ingredient can be determined according to standard pharmaceutical procedures in cell cultures and/or experimental animals, including, for example, determining the $LD_{50}$ (the dose lethal to 50% of the population, or for the methods of the invention, may alternatively by the kindling dose) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g. intravascular (intravenous, intraarterial, intracapillary) administration, injection into the cerebrospinal fluid, intracavity or direct injection in the brain. Intrathecal administration maybe carried out through the use of an Ommaya reservoir, in accordance with known techniques. (F. Balis et al., Am J. Pediatr. Hematol. Oncol. 11, 74, 76 (1989).

The effective amount of a therapeutic composition to be given to a particular patient will depend on a variety of factors, several of which will be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing $LD_{50}$ animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In another aspect of the invention, candidate agents are screened for the ability to improve cognitive impairment. Such compound screening may be performed using an in vitro model, a genetically altered cell or animal, or purified protein, particularly the human $GABA_A$ receptor or cells expressing such a receptor. A wide variety of assays may be used for this purpose. In one embodiment, compounds that are active in binding assays with the channel proteins, or are predicted to be antagonists of the receptor are then tested in an in vitro culture system. Alternatively, candidate agents are tested for GABAA chloride ionophore blocking activity, and may then be assessed in animal models for treatment of cognitive impairment. Drug testing may further assess the activity of a compound in kindling seizures or convulsions, where a compound with a broad dosage difference between the desired and undesired activity may be selected.

For example, candidate agents may be identified by known pharmacology, by structure analysis, by rational drug design using computer based modeling, by binding assays, and the like. Such candidate compounds are used to contact cells in an environment permissive $GABA_A$ channel function. Such compounds may be further tested in an in vivo model for improvement of cognitive impairment.

The term "agent" as used herein describes any molecule, e.g. protein or pharmaceutical, with the capability of modulating cognitive impairment by acting through neuronal inhibitory pathways. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Generally a plurality of assay mixtures are run in parallel with different agent concentrations to obtain a differential response to the various concentrations. Typically one of these concentrations serves as a negative control, i.e. at zero concentration or below the level of detection.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example.

Libraries of candidate compounds can also be prepared by rational design. (See generally, Cho et al., *Pac. Symp. Biocompat.* 305-16, 1998); Sun et al., *J. Comput. Aided Mol. Des.* 12:597-604, 1998); each incorporated herein by reference in their entirety). For example, libraries of GABA$_A$ inhibitors can be prepared by syntheses of combinatorial chemical libraries (see generally DeWitt et al., *Proc. Nat. Acad. Sci. USA* 90:6909-13, 1993; International Patent Publication WO 94/08051; Baum, *Chem. & Eng. News,* 72:20-25, 1994; Burbaum et al., *Proc. Nat. Acad. Sci. USA* 92:6027-31, 1995; Baldwin et al., *J. Am. Chem. Soc.* 117:5588-89, 1995; Nestler et al., *J. Org. Chem.* 59:4723-24, 1994; Borehardt et al., *J. Am. Chem. Soc.* 116:373-74, 1994; Ohlmeyer et al., *Proc. Nat. Acad. Sci. USA* 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing non-hydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Compounds that are initially identified by any screening methods can be further tested to validate the apparent activity. The basic format of such methods involves administering a lead compound identified during an initial screen to an animal that serves as a model for humans and then determining the effects on cognitive impairment. The animal models utilized in validation studies generally are mammals. Specific examples of suitable animals include, but are not limited to, primates, mice, and rats.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The following examples are offered by way of illustration and not by way of limitation.

EXPERIMENTAL

Investigation of CNS abnormalities and cognitive dysfunction in DS has been greatly facilitated by the development of a segmentally trisomic mouse model of DS: Ts65Dn. Ts65Dn mice are trisomic for segments of mouse chromosome 16 (Mmu 16) highly homologous to the long arm of hC21, including portions of the so-called DS "critical region." Ts65Dn orthologues of hC21 include APP and GRIK1, and extend along the length of Mmu16 to genes encoding myxovirus resistance-2 (Mx2) and zinc finger protein 295 (znf295; approximately 17 Mb of DNA containing 108 of the 225 genes catalogued to hC21). Phenotypically, Ts65Dn mice faithfully recapitulate some of the most salient and fundamental features of DS. The topography of craniofacial maldevelopment in Ts65Dn mirrors that observed in DS patients, with concomitant changes seen at the level of individual bones of the craniofacial skeleton. Likewise, Ts65Dn mice exhibit similar patterns of cerebellar atrophy during early postnatal development, a function of reduced granule cell density in the internal granule layer (IGL) of the cerebellum. The utility of Ts65Dn as a mouse model of DS is strengthened further by findings that detail nearly comprehensive deficits in Ts65Dn short- and long-term spatial memory, working memory, and reference memory, and is punctuated by findings detailing the age-related atrophy of basal forebrain cholinergic groups (BFCNs) in Ts65Dn mouse brain (first evident at 6 months of age), a characteristic of both human DS and human Alzheimer's disease (AD).

In the past decade, a handful of studies have ultrastructurally described, and functionally assessed synaptic connections in the brain of a mouse model of DS, Ts65Dn. Quantitative electron microscopy (EM) of Ts65Dn CNS has revealed a loss of asymmetric, excitatory synapses in Ts65Dn cortex relative to WT tissue, with a concurrent sparing of symmetric, inhibitory synapses. Reductions in the density of excitatory synapses, and in the ratio of excitatory-to-inhibitory signaling in the Ts65Dn brain, have been noted alongside compensatory increases in the synaptic apposition lengths of asymmetric and symmetric synaptic junctions. There may be a rearrangement of GABAergic inhibitory connections onto principal excitatory neurons that would hinder excitatory drive, demonstrating more conspicuous GABAergic innervation of dendritic spines in the Ts65Dn brain. Electrophysiologically, isolated Ts65Dn hippocampus has been shown to exhibit reduced induction and maintenance of LTP after delivery of an LTP-eliciting tetanus, decreased PPF in the perforant path, and dramatically enhanced LTD, all functional manifestations of poor circuit activity. Circulating levels of frontal cortical BDNF, a neurotrophic agent released in an activity-dependent manner, correlate directly with Ts65Dn performance in the radial-arm maze task.

See, for example, Olson et al., Down syndrome mouse models Ts65Dn, Ts1Cje, and Ms1Cje/Ts65Dn exhibit variable severity of cerebellar phenotypes. Developmental Dynamics, 230: 581-589 (2004). Escorihuela et al., Impaired short- and long-term memory in Ts65Dn mice, a model for Down syndrome. Neuroscience Letters, 247: 171-174 (1998). Demas et al., Spatial memory deficits in segmental trisomic Ts65Dn mice. Behavioral Brain Research, 82: 85-92 (1996). Holtzman et al., Developmental abnormalities and age-related neurodegeneration in a mouse model of Down syndrome. Proceedings of the National Academy of Science USA, 93: 13, 333-13, 338 (1996). Hyde and Crnic, Age-related deficits in context discrimination learning in Ts65Dn mice that model Down's syndrome and Alzheimer's disease. Behavioral Neuroscience, 115: 1239-1246 (2001). Hyde et al., Ts65Dn mice, a model for Down syndrome, have deficits in context discrimination learning suggesting impaired hippocampal function. Behavioural Brain Research, 118: 53-60 (2001). Bimonte-Nelson et al., Frontal cortex BDNF levels correlate with working memory in an animal model of Down syndrome. Behavioural Brain Research, 139: 47-57 (2003). Hunter et al., Behavioral comparison of 4 and 6 month-old Ts65Dn mice: Age-related impairments in working and reference memory. Behavioural Brain Research, 138: 121-131 (2003). Wenger et al. Operant conditioning in the Ts65Dn mouse: Learning. Behavior Genetics, 34: 105-119 (2004). Kurt et al., Synaptic deficit in the temporal cortex of partial trisomy 16 Ts65Dn mice. Brain Research, 858: 191-197 (2000). Siarey et al., Altered long-term potentiation in the young and old Ts65Dn mouse, a model for Down syndrome. Neuropharmacology, 36: 1549-1554 (1997). Siarey et al. Increased synaptic depression in the Ts65Dn mouse, a model for mental retardation in Down syndrome. Neuropharmacology, 38: 1917-1920 (1999).

The relative balance of excitation and inhibition in the brain, mediated respectively by the amino acid neurotransmitters glutamate and GABA, governs the assembly of neural circuits throughout development and the ability of the mature brain to undergo plastic responses thought to underlie adult learning and memory. Recent neuroanatomical and electrophysiological findings from a mouse model of Down syndrome (DS), Ts65Dn, suggest that cognitive impairment in the disorder arises from an offset of this critical balance, tilting decisively in favor of inhibition. Due to the tight convergence between structural and electrophysiological data suggesting excessive GABAergic inhibition in the Ts65Dn brain, we put together a program of study to assess the relationship between this overinhibition and learning deficits in Ts65Dn mice.

The results provided below indicate that increased GABAergic signaling does play a pivotal role in Ts65Dn learning deficits. Administration of picrotoxin (PTX) i.p., a quintessential non-competitive antagonist of the $GABA_A$ receptor that blocks chloride ionophore conductance, normalizes learning of Ts65Dn mice in an object recognition task when delivered chronically on a daily regiment, but not with acute application. Likewise, this improvement in Ts65Dn cognition is persistent, as PTX-treated animals maintain normal object recognition memory for at least 2 weeks post-treatment.

Subsequently the generality of this phenomenon was determined, and it was found that other compounds also thought to act as $GABA_A$ chloride ionophore blockers rescue Ts65Dn learning deficits in the object recognition task. The most clinically relevant of these, Metrazol, was administered via voluntary oral feeding in mice to mimic the most typical route of drug delivery in humans, and like PTX, was found to have longevity in its effects for weeks after treatment. Further data indicate that the effects of GABA-A antagonists in Ts65Dn mice are restricted to particular functionalities. Whereas PTX is able to recover Ts65Dn declarative memory in the object recognition test, a rodent cognitive task that requires the integrity of higher-order brain areas in the cortex and hippocampus, the drug does not influence Ts65Dn motor learning in an accelerating rotorod test, a task that requires the integrity of the cerebellum.

These results demonstrate that mental retardation in DS can be amenable to pharmacological treatment, with compounds that have had a history of clinical use. It is believed that chronic, repetitive exposure to low doses of $GABA_A$ chloride ionophore blockers is causing semi-permanent circuit rewiring that allows for greater circuit efficacy in higher order brain areas, and better learning and memory. This interpretation is in agreement with data showing that acute exposure to these same drugs does not lead to reliable improvements in Ts65Dn memory, and that Ts65Dn cognitive improvement during chronic drug administration is subsequently maintained after the cessation of drug treatment. It is further bolstered by data in normal rodents, where chronic, yet circumscribed, regiments of GABA antagonists are also able to exert beneficial effects on cognition that outlive the timing of drug application. In the context of clinical research, these findings translate into drug regimens that can begin in children with DS at early adolescence, extending into early adulthood, and that would be monitored via modern neuropsychological testing and non-invasive functional imaging.

Methods and Results

The object recognition task, a behavioral assay not requiring explicit rule learning or prolonged training, is based on the innate tendency of mice to differentially explore novel objects over familiar ones. Animals are submitted to daily handling sessions and are given an opportunity to habituate to a black acrylic, boxed enclosure, where they are exposed to two different objects during a 15-min training session. These objects are made from various nonporous materials (ceramic, metal, glass, etc.), and possess various color schemes. All are generally consistent in height and volume, and are symmetrical on a horizontal plane. They are set in two corners of the apparatus, positioned across from one another along its diameter. Subsequently, a 15-min. testing session is conducted 24 h after training. Here, the mice are presented with the object they had explored the previous day, and a new item (the objects being alternatively positioned in one corner or another in a balanced fashion).

Memory is operationally defined as the proportion of time animals spend investigating the novel object minus the proportion spent investigating the familiar one (Discrimination Index, DI=[Novel Object Exploration Time/Total Exploration Time−Familiar Object Exploration Time/Total Exploration Time]×100), where exploration constitutes any investigative behavior (i.e., head orientation, sniffing) or deliberate contact (i.e. rearing, licking) that occurs with each object. Behavioral trials are recorded by a tripod-mounted digital camera. Importantly, the object recognition task can be used repeatedly to evaluate rodent memory across time, and across various drug treatment regiments. Mice are trained and tested once per week, each experimental session separated by a 1-week interval, and are serially presented with new sets of objects. In this scheme, each mouse is considered a naïve subject, and each week's performance is considered an independent observation. Finally, all behavioral data are analyzed by Student's unpaired t tests.

The object recognition test has been shown to reliably distinguish drug-induced effects on memory in rodents. Moreover, learning performance in the test is not confounded by task aversiveness, a variable common in avoidance paradigms, in food-motivated tasks, and in the Morris water maze (MWM). This is critical when evaluating Ts65Dn mouse learning and memory, as Ts65Dn mice are naturally more emotionally labile than WT mice, and their performance in cognitive tests has been demonstrated to be disproportionately influenced by stress. Additionally, rodent execution of the object recognition task does not involve strenuous or highly coordinated movement, a requirement that can also potentially confound Ts65Dn performance in tests like the MWM, as Ts65Dm mice exhibit abnormal gait dynamics. Thus, object recognition is an appropriate rodent cognitive task to assess Ts65Dn learning and memory deficits, and the mitigation of these deficits with pharmacological treatment. Importantly, object recognition is a test that can also be directly translated to humans, as children with DS exhibit difficulties in a humanized version of the task.

Shown in FIG. 1. Chronic Administration of PTX or BB Rescues and Maintains Ts65Dn Object Recognition Memory. The present experiment was carried out in a longitudinal, cross-over fashion, submitting four cohorts of WT and Ts65Dn experimental pairs to a 4-week testing schedule. (A) Here, WT and trisomic mice were randomly assigned to groups receiving daily injections of saline or PTX (1 mg/kg), and were submitted to two repetitions of object recognition testing (Weeks 1-2). Note that untreated WT and Ts65Dn pairs had been previously run in order to validate the 2-object recognition test. As expected, untreated and saline-injected Ts65Dn mice had lower DI scores than their WT counterparts ($p<0.04$ and $p<0.05$, respectively; n=14-18 for each genotype in the untreated or saline condition). However, Ts65Dn mice chronically administered PTX performed cognitively at levels comparable to untreated WT mice ($p=0.50$) and to WT mice receiving chronic saline ($p=0.16$) or PTX ($p=0.38$; n=9-10 for each genotype treated with PTX). (B) Subsequently, saline-injected WT and Ts65Dn mice were randomly segregated into groups that would continue to receive daily saline injections during the third and fourth repetitions of object recognition testing, or into groups that would undergo daily picrotoxin injections during the second testing period (Weeks 3-4). WT and Ts65Dn mice that had been chronically administered PTX, now received daily injections of saline. Not surprisingly, Ts65Dn mice continuing to receive saline had significantly lower DI scores than WT mice also continuing to receive saline ($p<0.05$; n=6 for each genotype in this condition), than WT mice receiving PTX for the first time ($p<0.02$), and lower scores than WT mice having been kindled with PTX ($p<0.10$). Conversely, Ts65Dn mice undergoing chronic PTX administration for the first time (n=8-9 for each genotype in this condition), showed no significant differences from WT mice continuing to receive saline ($p=0.21$), from WT mice also newly submitted to the chronic PTX regiment ($p=0.18$), or to WT mice having underwent kindling in weeks 1-2 ($p=0.41$). Interestingly, kindled Ts65Dn mice (n=6-7 for each genotype having undergone kindling and now receiving saline) exhibited similar object recognition performance as WT mice in all treatment conditions ($p=0.23$, $p=0.20$, and $p=0.43$, for comparisons with saline, PTX, and kindled groups, respectively), and resembled Ts65Dn mice given daily PTX for the first time ($p=0.48$). Finally, Ts65Dn mice receiving bilobalide (BB) throughout the 4-week testing schedule (30 daily i.p. injections total; n=14-18 for each genotype in this treatment condition), resembled Ts65Dn mice receiving PTX. N values reflect the number of observations (repetitions) per treatment. DI values are expressed as mean±SEM.

Figure 2:
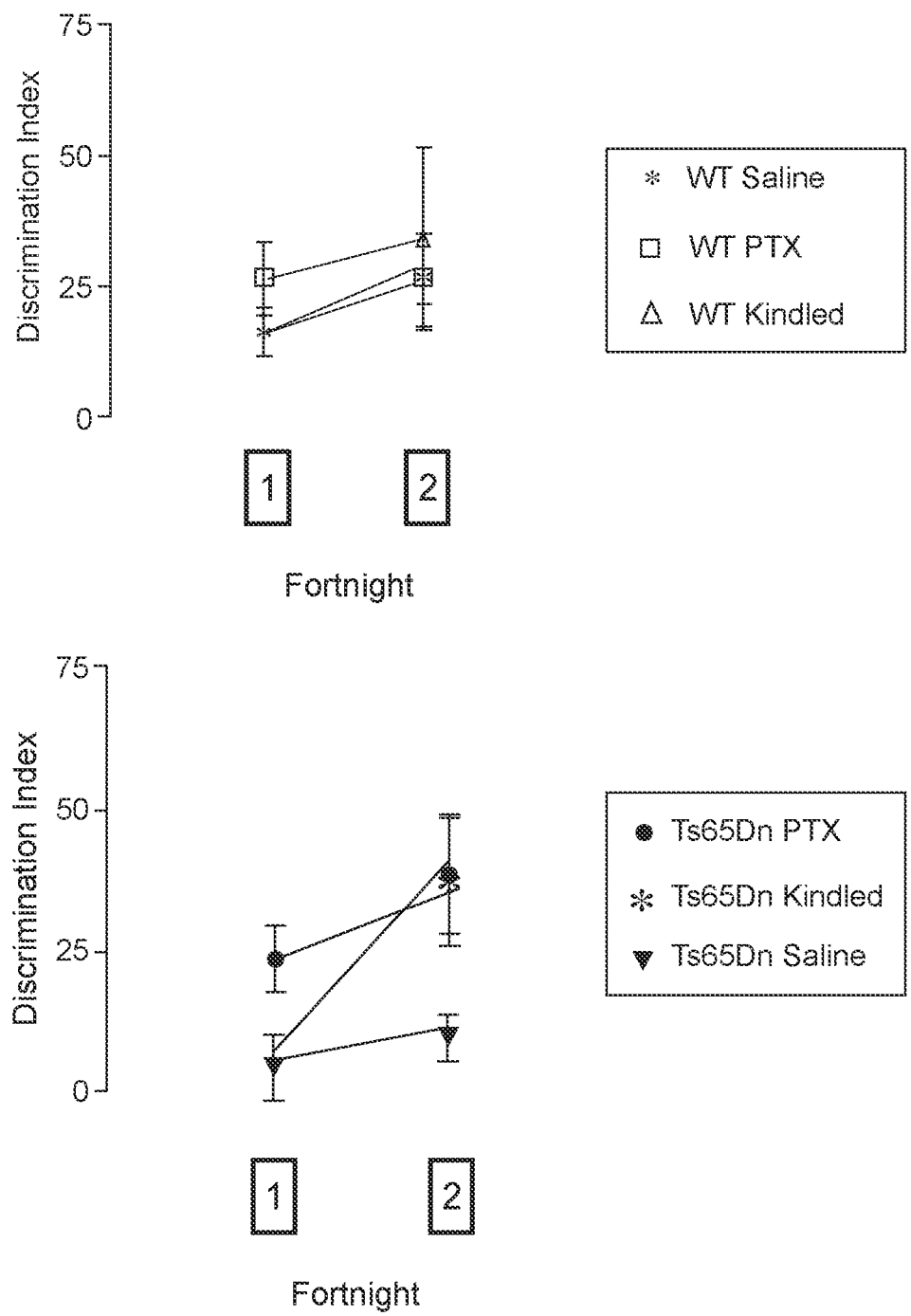
FIG. 2. Topography of WT and Ts65Dn Object Recognition Performance before and after Drug Treatment with PTX.
Figure 3:
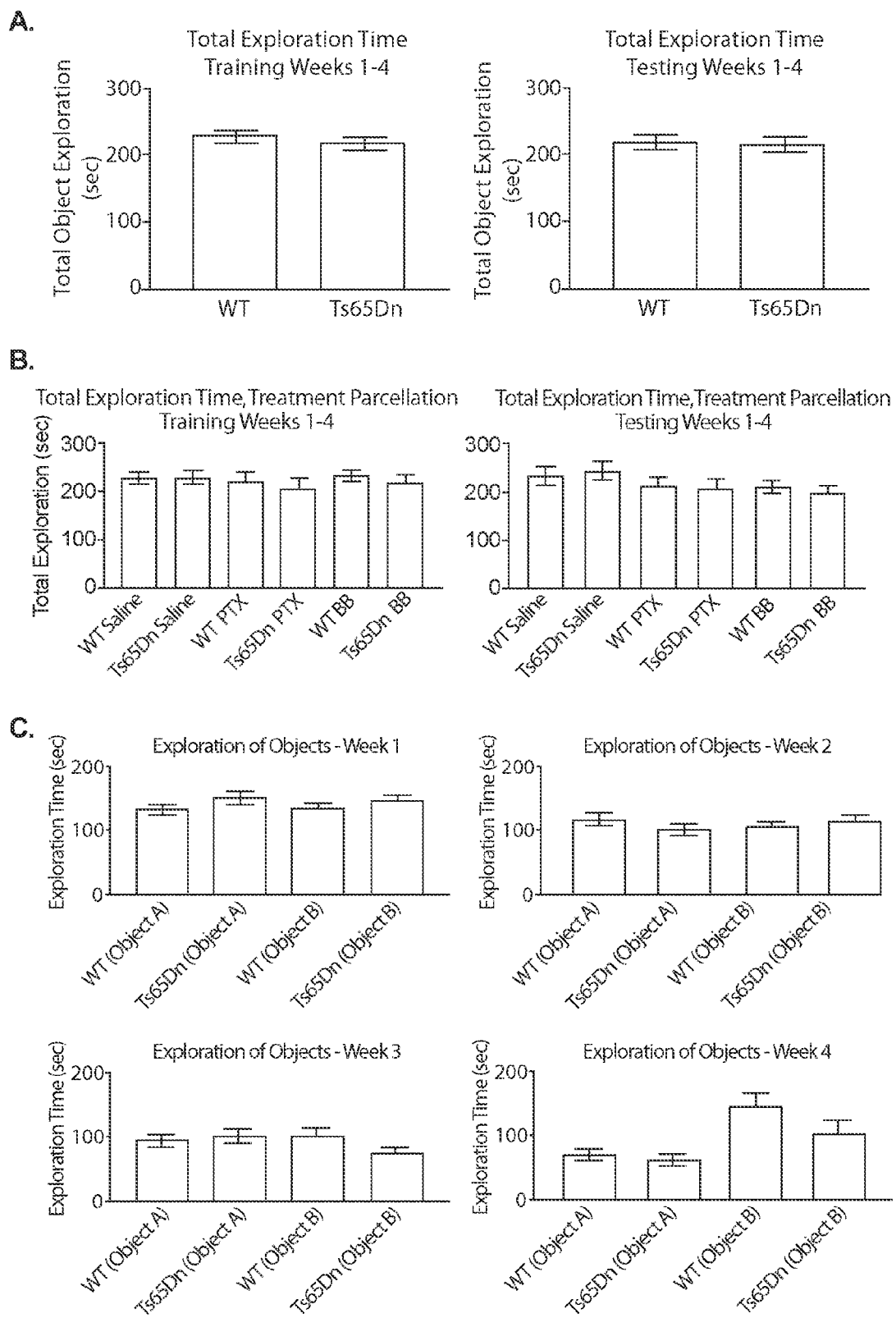
FIG. 3A-3C. PTX and BB, Control Data.

Shown in FIG. 2. Topography of WT and Ts65Dn Object Recognition Performance before and after Drug Treatment with PTX. In FIG. 3. PTX and BB, Control Data: All mice in the object recognition experiment were exposed to standardized sets of objects presented serially each week in a uniform fashion. Note that WT and Ts65Dn mice showed nearly identical amounts of total object exploration time during the object recognition training and testing periods spread across the 4-week schedule of object recognition testing, spending invariably 20-25% of their experimental sessions investigating objects (FIG. 3A). Total object exploration was not influenced by genotype or by treatment regiment (FIG. 3B). Likewise, with the exception of Week 4, neither WT or Ts65Dn mice exhibited an object bias during the four individual training sessions conducted weekly across the 4-week testing schedule, spending similar amounts of time with each familiar object encountered during the training period (FIG. 3C). Notably, the exploration bias in Week 4 occurred to the same degree in both WT and Ts65Dn mice, suggesting similar mnemonic encoding during the 15-min training session. Values are expressed as mean±SEM.

Figure 4:
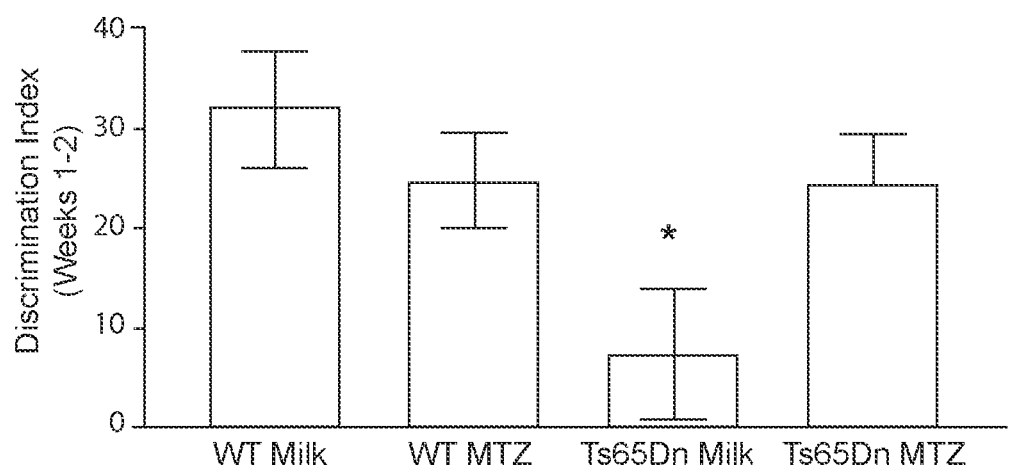
FIG. 4. Like PTX and BB, Metrazol improves Ts65Dn memory in the object recognition task.

Shown in FIG. 4. Like PTX and BB, Metrazol improves Ts65Dn memory in the object recognition task. WT and Ts65Dn mice were handled, habituated, and tested as outlined in experiments with PTX and BB. The animals were randomly assigned to groups receiving daily servings of chocolate milk or Metrazol (3 mg/kg), and were submitted to two repetitions of object recognition testing. For the purposes of drug delivery, all mice were conditioned to drinking chocolate milk in their home cages and then in cylindrical feeding tubes for 4 days. Subsequent to this conditioning, they were placed daily into the feeding tubes, and presented with small eppendorf caps of milk or a milk-Metrazol cocktail. The milk solutions were typically consumed within 10 min, after which the mice were returned to their home cages. In the current experiment, two cohorts of WT and Ts65Dn mice were submitted to a two week testing schedule. Consistent with the PTX and BB experiments, Ts65Dn mice receiving milk (n=18) exhibited impaired object recognition performance relative to WT mice also receiving milk (n=18; $p<0.004$) or WT mice receiving Metrazol (n=20; $p<0.02$). However, Ts65Dn given daily servings of Metrazol (n=19) had DI scores on par with those of WT mice given milk ($p<0.16$) or Metrazol ($p<0.47$), and had scores that were significantly higher than Ts65Dn mice administered milk alone ($p<0.03$). N values reflect the number of observations (repetitions) per treatment. DI values are expressed as mean±SEM.

Figure 5:
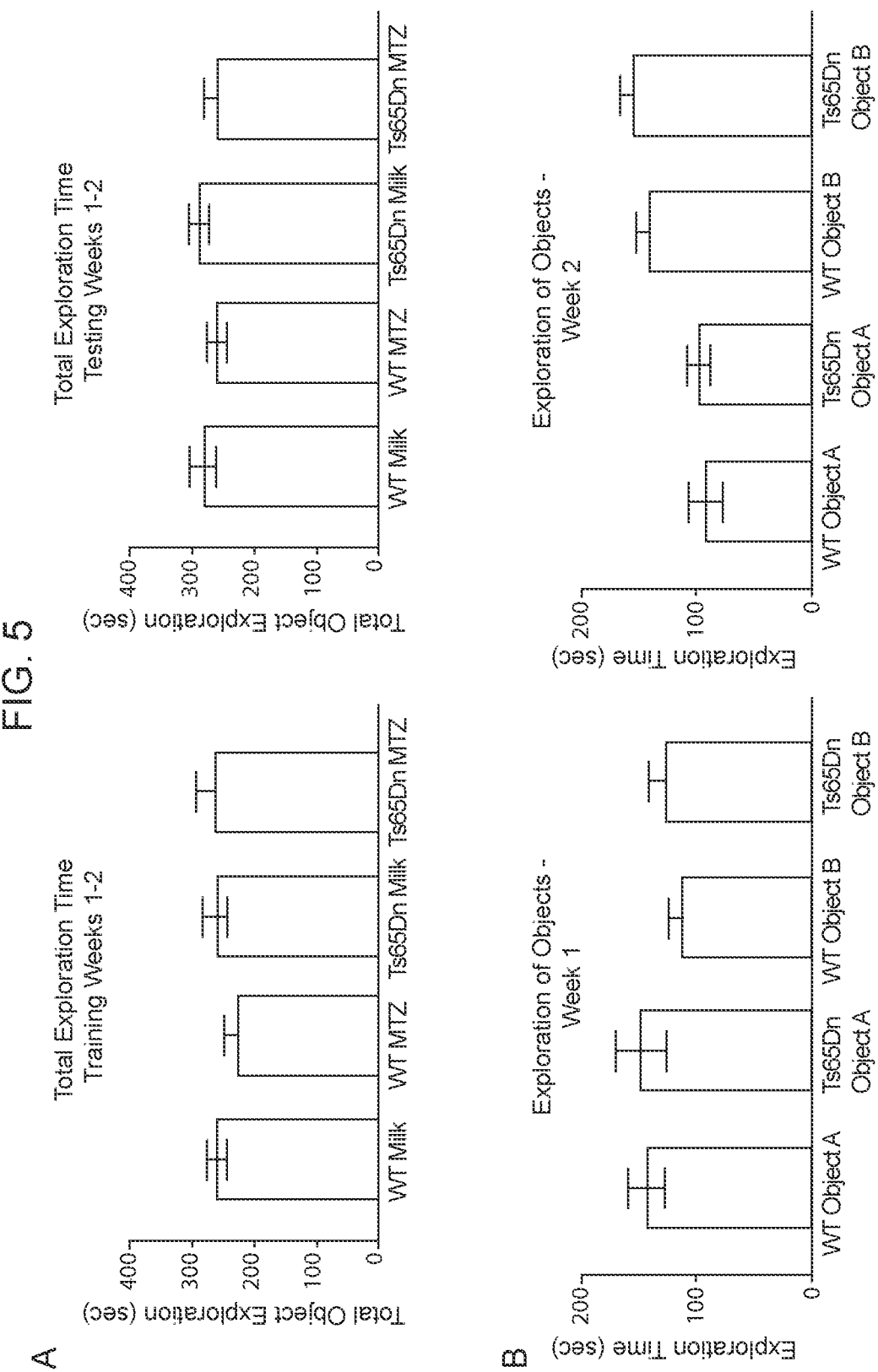
FIG. 5A-5B. MTZ, Control Data.

Shown in FIG. 5. MTZ, Control Data. Total object exploration during the training and testing periods, was unaffected by genotype or by milk-MTZ treatment (FIG. 5A). Exploration of individual familiar objects during the training sessions, likewise, was similar across all the treatment conditions, but for a slight object bias in Week 2 (FIG. 5B). Values are expressed as mean±SEM.

Figure 6:
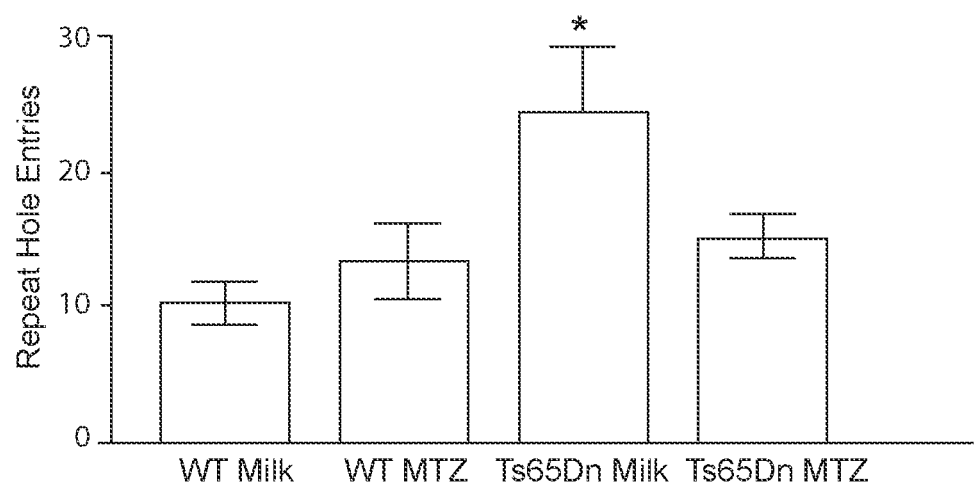
FIG. 6. The Effects of Metrazol on Ts65Dn Cognitive Behavior, like those of PTX, are Long-Lasting.

Shown in FIG. 6. The Effects of Metrazol on Ts65Dn Cognitive Behavior, like those of PTX, are Long-Lasting. One cohort of WT and Ts65Dn mice, used to determine the effects of chronic Metrazol on Ts65Dn object recognition performance, were submitted to a spontaneous holeboard task approximately 1 month after the end of Metrazol treatment and object recognition testing. Here, milk- and drug-treated animals (now 5.0 months of age) were habituated to Med Associates open field activity monitors (27.9 cm×27.9 cm) (FIGS. 7b and 7c), and then evaluated for holeboard exploration during a 7-min session. Please note that 2 rounds of holeboard testing were conducted during the light phase of the light/dark cycle, and were separated by a 1-week interval. As would be predicted from results in the object recognition test, Ts65Dn mice formerly given milk (n=10) exhibited decreased exploration "efficiency," showing a greater number of head-dips into previously explored holes, relative to WT mice also formerly given milk (n=6; $p<0.03$) or WT mice that had been treated with Metrazol (n=12; $p<0.04$). In contrast, Ts65Dn mice that had received Metrazol (n=14) showed similar exploration efficiency ($p>0.07$ and $p<0.31$, for comparisons with WT-milk and WT-Metrazol groups, respectively). N values reflect the number of observations (repetitions) per treatment. Values are expressed as mean±SEM.

Figure 7:
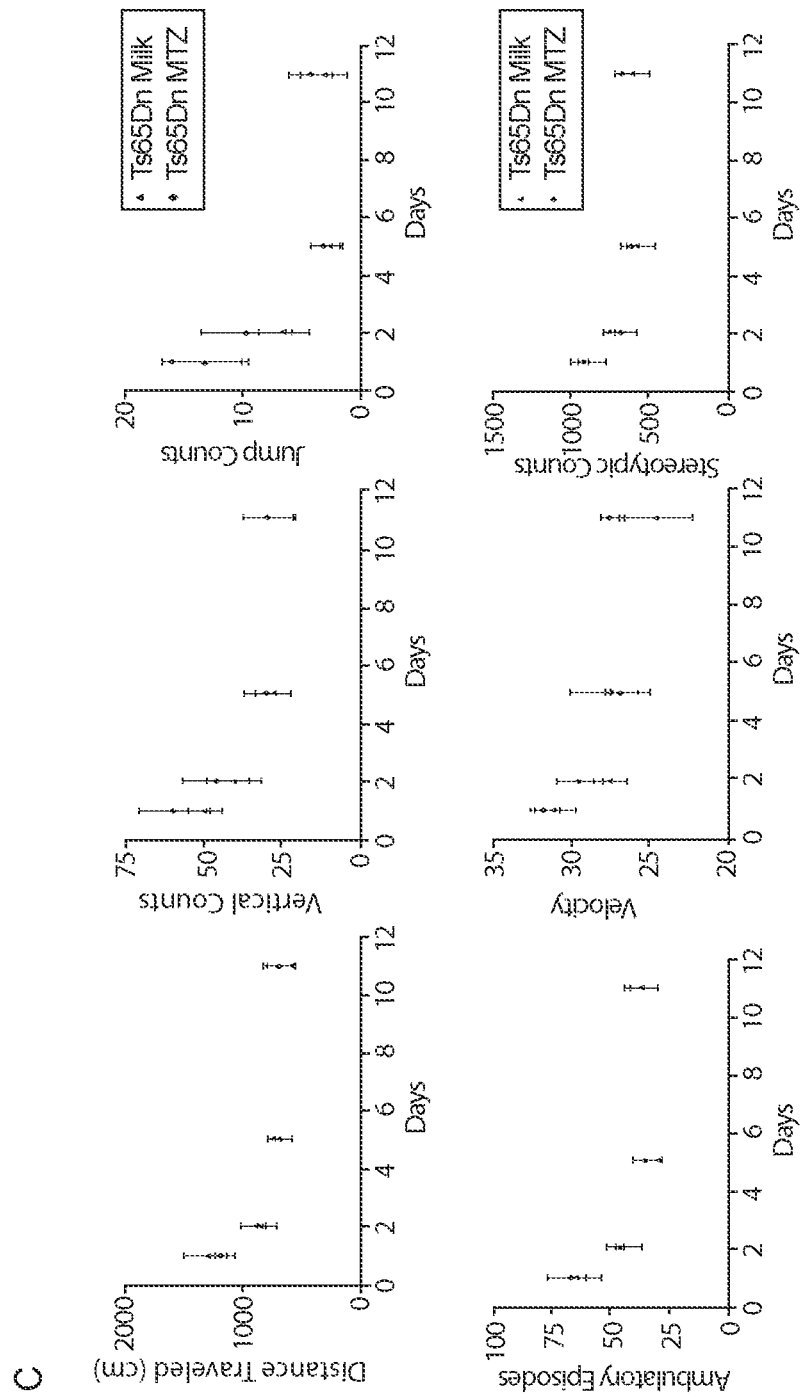
FIG. 7A-7C. WT and Ts65Dn Locomotor Habituation during the Light Cycle, and Indices of Mouse Habituation to the Med Associates Activity Monitors.
Figure 8:
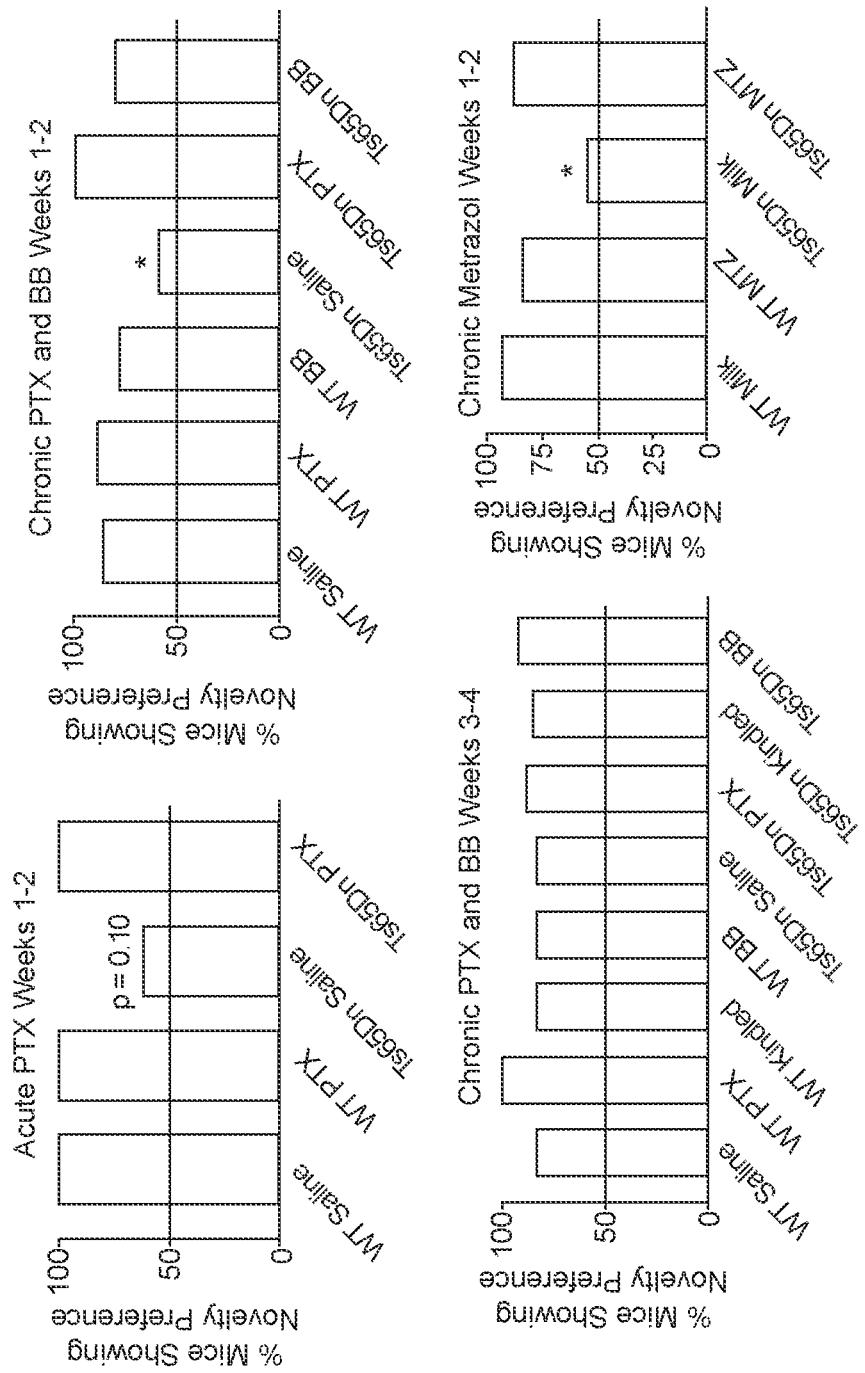
FIG. 8. Absolute Object Novelty Preference among Vehicle- and Drug-Treated WT and Ts65Dn Mice.
Figure 9:
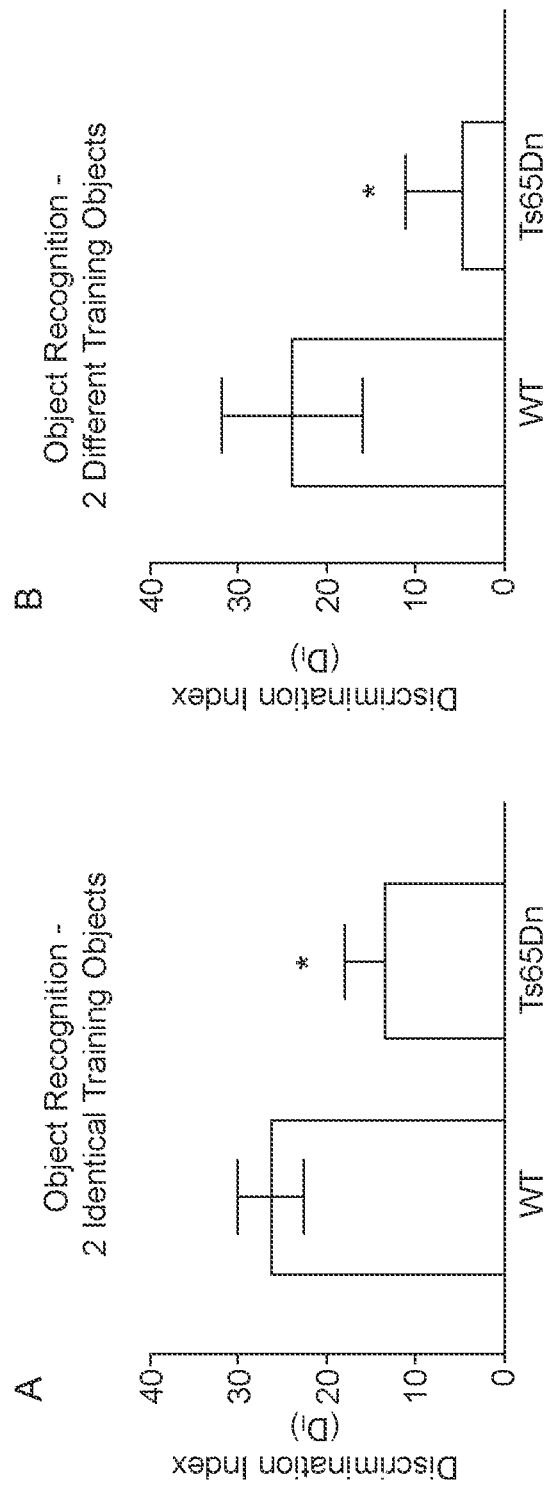
FIG. 9A-9B. Object Recognition Validation: One-Object Based and Two-Object Based Tasks.

Shown in FIG. 7. WT and Ts65Dn Locomotor Habituation during the Light Cycle, and Indices of Mouse Habituation to the Med Associates Activity Monitors. (A) One cohort of WT and Ts65Dn mice (n=6 for each genotype), naïve to drug treatment, was evaluated for habituation to a novel cage environment during the light cycle. Here, the number of central line crossings between the left half and the right half of the cage, were tabulated over 1 h. Consistent with previous literature, WT and Ts65Dn mice exhibited nearly identical declines in locomotor activity over the 1-h evaluation period. Values are expressed as mean±SEM. (B) Milk-fed and MTZ-treated WT and Ts65Dn mice, prior to holeboard testing (FIG. 6), exhibited similar indices of activity habituation to the Med Associates automated open field across 4 staggered sessions (the last 2 sessions separated by a ~1 week interval), suggesting that the increase in repeat hole entries exhibited by milk-fed Ts65Dn mice was not a byproduct of general hyperactivity. Values are expressed as mean±SEM. (C) A closer look at Ts65Dn habituation in the Med Associates automated open field reveals particular similarities between milk- and MTZ-treated Ts65Dn mice, further stipulating a cognitive component for the differences observed between milk- and drug-treated, trisomic animals in the holeboard task. Values are expressed as mean±SEM. FIG. 8. Absolute Object Novelty Preference among Vehicle- and Drug-Treated WT and Ts65Dn Mice. FIG. 9. Object Recognition Validation One-Object Based and Two-Object Based Tasks.

Figure 10:
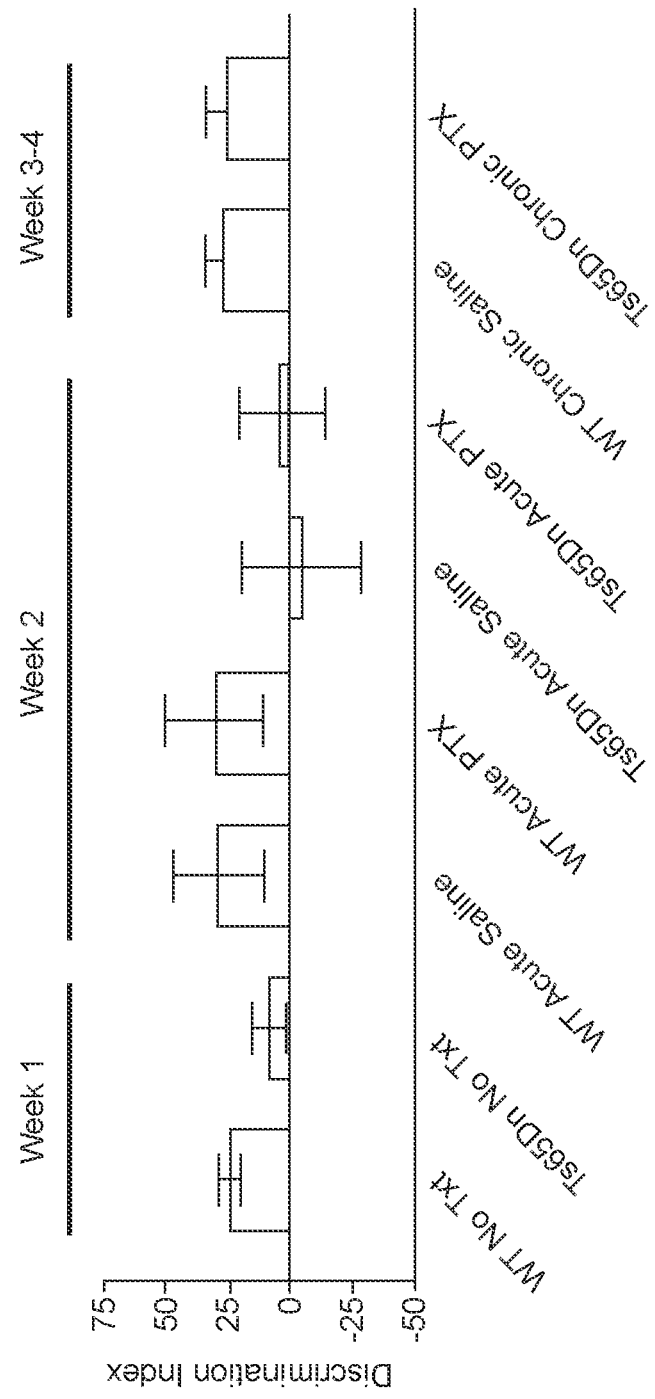
FIG. 10. Chronic, but not Acute, Application of PTX Restores Ts65Dn Object Recognition Memory in a One-Object Based Task.
Figure 11:
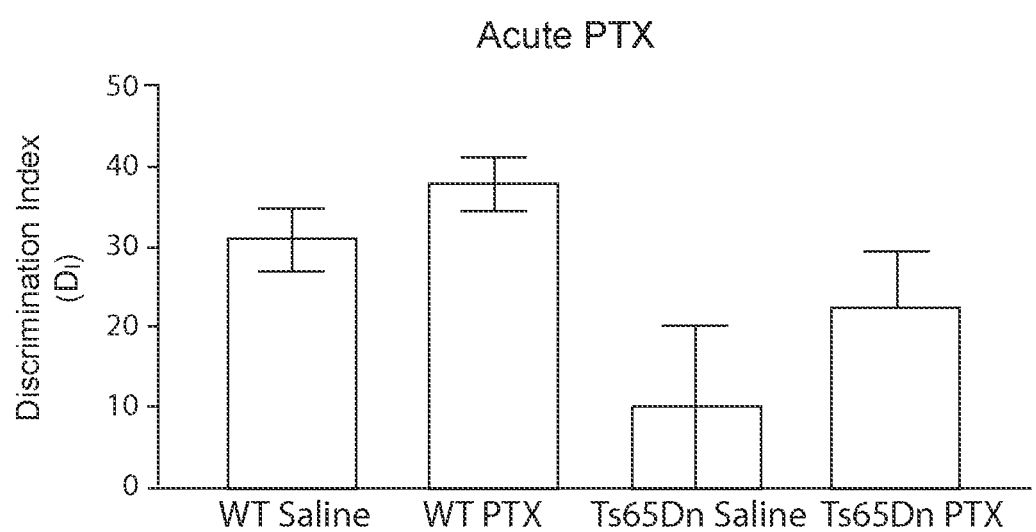
FIG. 11. Acute PTX is Unable to Reliably Rescue Ts65Dn Performance in a 2-Object Based Object Recognition Test.

Shown in FIG. 10. Chronic, but not Acute, Application of PTX Restores Ts65Dn Object Recognition Memory in a One-Object Based Task. In the current experiment, a cohort of WT and Ts65Dn mice (n=6 for each genotype) was evaluated in the object recognition task across 4 sequential weeks. In the first week, untreated WT mice exhibited significantly higher DI scores than untreated Ts65Dn mice ($p<0.05$), whose scores were not statistically different from zero (p=0.31). In the second week, WT and Ts65Dn were randomly assigned to control and drug treatment groups (n=3 for each genotype/treatment group). Animals received an acute injection of saline or picrotoxin (PTX; 1 mg/kg) immediately after object recognition training, and the effects of these treatments were evaluated 24-h later during object recognition testing. Here, WT and Ts65Dn mice exhibited performances, on average, similar to those in Week 1, suggesting that acute PTX is unable to improve memory in WT mice and is unable to rescue memory deficits in Ts65Dn mice. Subsequently, in preliminary work, we evaluated the ability of chronic PTX administration to ameliorate Ts65Dn object recognition performance in Weeks 3 and 4. Indeed, daily injections of PTX (1 mg/kg) in Ts65Dn mice (n=6; 12 observations total), beginning a day after Week 2 testing and conducted on object recognition training days right after the training session, were able to increase Ts65Dn performance to the level of WT mice receiving daily injections of saline (n=6; 12 observations total). Shown in FIG. 11. Acute PTX is Unable to Reliably Rescue Ts65Dn Performance in a 2-Object Based Object Recognition Test. Shown in FIG. 12. Motor Learning in WT and Ts65Dn Mice: Chronic PTX Treatment does not influence Ts65Dn Rotorod Performance.

In summary, these data demonstrate that Picrotoxin, a non-competitive $GABA_A$ receptor antagonist and chloride ionophore blocker, normalizes object recognition memory in Ts65Dn mice at 3 month of age with chronic, but not acute, administration. Improved Ts65Dn learning with PTX is maintained post drug treatment. Other non-competitive $GABA_A$ antagonists that directly block chloride conductance, namely Metrazol and Bilobalide, also restore Ts65Dn object recognition performance with chronic application. Other aspects of cognition, such as holeboard exploration efficiency, are rescued and persevere in Ts65Dn mice after GABA antagonist treatment with Metrazol. The effects of GABA antagonists on Ts65Dn learning and memory are restricted to specific functionalities; whereas they improve Ts65Dn object recognition and exploration efficiency, they do not influence Ts65Dn motor learning.

Example 2

Mental retardation (MR) remains a prevalent form of non-progressive cognitive impairment, affecting 2-3% of the population in the industrialized world. Disorders involving MR, though narrowly defined by an IQ<70 and by deficits in academic, adaptive and interpersonal skills, are nonetheless spread over a broad etiology resulting from both genetic and non-genetic causes. The breadth and frequency of MR-related cognitive dysfunction is alarming considering that pharmacological intervention is currently non-existent. Historically, neuroscientists have probed the brain in MR for clues to possible treatment strategies for MR-related learning difficulties. In the case of Down syndrome, these pioneering investigations have led to observations of neuronal cell loss, stunted dendritic branching, and spine dysgenesis. Interestingly, many of the histological features noted in the brains of individuals with Down syndrome parallel phenotypes that have been found in the brains of individuals with other classes of MR, such as inborn errors of metabolism and non-genetic insults. Connections among different X-linked forms of MR have also been made, with disrupted synaptic structure, synaptic plasticity, and Ras-MAPK signaling as emerging themes. Similarities across the wide spectrum of MR-related disorders argue that common mechanisms underlie the manifestation of learning and memory deficits in intellectually handicapped children and young adults.

The data provided above indicate that MR is the byproduct of long-term changes in neural excitability, driven by increases in the contribution of inhibition to neural circuits, which is treated by "therapeutic kindling".

Traditional forms of synaptic plasticity (i.e., long-term potentiation and long-term depression) occur in the context of stabilizing forces that allow a circuit to maintain a physiologically relevant level of activity. That way, the circuit does not spiral into excessive excitation or total quiescence. These compensatory mechanisms, collectively referred to as "homeostatic plasticity," occur over broad time scales, and then, only in response to chronic excitation or inhibition of neuronal networks.

Homeostatic plasticity is observed at virtually all levels of hierarchical organization in the mammalian brain. At the broadest level, chronic changes in central nervous system (CNS) activity can directly modify the cellular composition of a neural circuit, setting the ratio of inter-neurons to principal cells. It can also reconfigure established circuits with a defined cellular composition by manipulating the degree of connectivity between inhibitory and excitatory elements in the circuit. Beyond these alterations, homeostasis of neuronal activity may be achieved by changes in the molecular composition and the morphology of synapses. Molecular changes occurring at the synaptic level can involve scaling responses of α-amino-3-hydroxy-5-methyl-4-isoxazolepropionic acid (AMPA) and N-methyl-D-aspartic acid (NMDA) receptors, their membrane-associated guanylate kinase like (MAGUK) adaptors (i.e., PSD-95 and SAP102), and γ-aminobutyric acid A ($GABA_A$) receptors. Alternatively, morphological change can occur with the shape of postsynaptic dendritic spines.

The mammalian brain has been adapted with a comprehensive set of mechanisms integrated at the circuit, single-cell, and molecular level that functions to maintain a specific range of neuronal activity. The drive to conserve activity in neuronal networks, particularly in those that comprise the neocortex and hippocampus, suggests that an inability to properly balance excitation and inhibition would lead to neurological disorder and cognitive impairment, and various forms of MR have been attributed to the over-inhibition of neural circuits. Such a state is expected to compromise the capacity of the circuit to undergo Hebbian forms of associative plasticity (LTP, PPF) thought to underlie learning and memory.

The term "kindling" refers to an animal model of epileptogenesis, in which the periodic introduction of an initially sub-convulsive electrical or chemical stimulus to the brain progressively leads to electrographic and behavioral seizure activity (Goddard (1967) Nature 214, 1020-1021). Once in this state, animals show a permanent (lifetime) enhancement in their sensitivity to stimulus-induced seizures, suggesting that the synaptic responsiveness of the stimulated circuits undergoes an augmentation that persists in the absence of further reinforcement (McNamara et al. (1980) Prog. Neurobiol. 15, 139-159). The long-lasting properties of kindling suggest that it is a model of neural plasticity. In keeping with this suggestion, kindling via repetitive site-specific electrical stimulation or repetitive systemic administration of high doses of $GABA_A$ receptor antagonists (typically pentylenetetrazole; PTZ, see Mason and Cooper (1972) Epilepsia 13, 663-674), shares characteristics with LTP (Malenka (2003) Nat. Rev. Neurosci. 4, 923-9267), the foremost synaptic model of learning and memory. Each phenomenon is dependent on NMDA receptor activation, protein synthesis, and on specific patterns of stimulation for proper induction. Likewise, kindling and LTP both demonstrate some degree of specificity. While the effects of LTP are restricted to neural circuits that are directly stimulated, the effects of kindling extend only along circuits that are synaptically linked.

However, there are significant differences between kindling and LTP. Whereas the functional consequence of LTP is the incorporation of AMPA receptors at synaptic sites, that of kindling seems to be the gross removal of GABAergic inhibition from stimulated and adjoining circuits (Stelzer et al., (1987) Nature 326, 698-701). Indeed, electrical stimulation, or chronic administration of PTZ, has been continually shown to result in decreased electrophysiological or biochemical indices of GABAergic function.

The close correspondence between kindling and epilepsy in animals has created the perception that kindling is pathological to the CNS, despite the fact that the neuronal interactions that are catalyzed in response to kindling are presumed to be available to the normal brain.

The data provided in Example 1 demonstrates the use of low doses of an agent that can cause kindling, i.e. "therapeutic kindling" doses, to treat an animal model for DS. It is shown that chronic (but not acute) once a day drug administration in Ts65Dn mice was able to normalize cognitive performance in the novel object recognition and spontaneous alteration tasks, and to rescue hippocampal LTP (see also Fernandez et al., (2007) Nat. Neurosci. 10, 411-413, herein specifically incorporated by reference). Importantly, PTZ led to a persistent, post-drug recovery of Ts65Dn cognition and LTP lasting for several months, demonstrating that the regimen induced long-term neuroadaptations in the hippocampus.

The efficacy of therapeutic kindling in Ts65Dn DS mice provides a process with widespread clinical utility. Traditionally, MR disorders have been unresponsive to pharmacological interventions, perpetuating the notion that they are treatment-resistant vestiges of abnormal brain development. The data on adult mice, however, indicates that this is not the case. The findings also point to the possibility that mature, but faulty circuits in MR, can be reopened from their present adult configuration and rewired to increase synaptic plasticity. If so, therapeutic kindling could be a frontline mechanism of adaptive change that could overturn MR in affected individuals, restoring to them a sense of self and improving their quality of life.

It is evident from the above results and discussion that improved methods for treating cognitive impairment are provided. The subject methods provide an effective means for improving cognitive function, particularly in individuals suffering from cognitive impairment disorders, e.g., Down syndrome, etc. As such, the subject methods represent an important contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for improving a cognitive function in a human with Down syndrome, the method comprising administering a single pharmaceutical active agent consisting of pentylenetetrazole to the human with Down syndrome, wherein not more than 3 mg pentylenetetrazole per kilogram body weight is administered to the human with Down syndrome per day for at least two weeks.

2. The method of claim 1, wherein at least about 0.1 mg/kg to not more than about 2 mg/kg pentylenetetrazole is administered to the human with Down syndrome per day.

3. The method of claim 1, wherein the cognitive function is selected from the group consisting of memory impairment and learning ability impairment.

4. The method of claim 1, wherein the pentylenetetrazole is administered daily for at least about one year.

5. The method of claim 1, wherein the pentylenetetrazole is orally administered to the human.

6. The method of claim 5, wherein the pentylenetetrazole is administered once per day.

7. The method of claim 6, wherein the pentylenetetrazole is administered in a pharmaceutical composition comprising an inactive ingredient.

8. A method for improving a cognitive function in a human with Down syndrome, the method comprising administering a single pharmaceutical active agent consisting of pentylenetetrazole to the human with Down syndrome at a dose less than about 0.1 times the kindling dose in humans, wherein the dose is administered once per day for at least two weeks.

9. The method of claim 8, wherein the dose is less than 0.05 times the kindling dose.

* * * * *

UNITED STATES PATENT AND TRADEMARK OFFICE
CERTIFICATE OF CORRECTION

| | | |
|---|---|---|
| PATENT NO. | : 8,729,067 B2 | Page 1 of 1 |
| APPLICATION NO. | : 11/752188 | |
| DATED | : May 20, 2014 | |
| INVENTOR(S) | : Garner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this
Eleventh Day of August, 2015

Michelle K. Lee
*Director of the United States Patent and Trademark Office*